United States Patent
Hackel et al.

(10) Patent No.: US 10,287,572 B2
(45) Date of Patent: May 14, 2019

(54) PROTEIN SCAFFOLDS AND METHODS OF USE

(71) Applicant: REGENTS OF THE UNIVERSITY OF MINNESOTA, Minneapolis, MN (US)

(72) Inventors: Benjamin Joseph Hackel, Edina, MN (US); Max Anthony Kruziki, St. Paul, MN (US); Sumit Bhatnagar, Ann Arbor, MI (US); Hong Zhou, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 0 days.

(21) Appl. No.: 15/032,753

(22) PCT Filed: Oct. 31, 2014

(86) PCT No.: PCT/US2014/063441
§ 371 (c)(1),
(2) Date: Apr. 28, 2016

(87) PCT Pub. No.: WO2015/066480
PCT Pub. Date: May 7, 2015

(65) Prior Publication Data
US 2016/0244745 A1 Aug. 25, 2016

Related U.S. Application Data

(60) Provisional application No. 61/898,723, filed on Nov. 1, 2013, provisional application No. 62/017,470, filed on Jun. 26, 2014.

(51) Int. Cl.
| | | |
|---|---|---|
| C12N 7/00 | (2006.01) | |
| A61K 38/00 | (2006.01) | |
| A61K 38/16 | (2006.01) | |
| C12N 15/10 | (2006.01) | |
| C07K 14/005 | (2006.01) | |

(52) U.S. Cl.
CPC ........ *C12N 15/1044* (2013.01); *A61K 38/162* (2013.01); *C07K 14/005* (2013.01); *C12N 7/00* (2013.01); *A61K 38/00* (2013.01); *C12N 2795/10222* (2013.01); *C12N 2795/10232* (2013.01)

(58) Field of Classification Search
None
See application file for complete search history.

(56) References Cited

U.S. PATENT DOCUMENTS

| | | |
|---|---|---|
| 4,880,078 A | 11/1989 | Inoue et al. |
| 5,128,326 A | 7/1992 | Balazs et al. |
| 5,290,540 A | 3/1994 | Prince et al. |
| 5,679,377 A | 10/1997 | Bernstein et al. |
| 5,855,913 A | 1/1999 | Hanes et al. |
| 5,874,064 A | 2/1999 | Edwards et al. |
| 5,912,015 A | 6/1999 | Bernstein et al. |
| 5,916,597 A | 6/1999 | Lee et al. |
| 5,934,272 A | 8/1999 | Lloyd et al. |
| 5,985,309 A | 11/1999 | Edwards et al. |
| 5,985,320 A | 11/1999 | Edwards et al. |
| 5,989,463 A | 11/1999 | Tracy et al. |
| 6,019,968 A | 2/2000 | Platz et al. |
| 6,316,024 B1 | 11/2001 | Allen et al. |
| 6,350,466 B1 | 2/2002 | Li et al. |
| 8,221,765 B2 * | 7/2012 | Camphausen ......... C07K 14/78 424/192.1 |
| 2008/0108798 A1 | 5/2008 | Lipovsek et al. |
| 2012/0302492 A1 | 11/2012 | Harkins et al. |

FOREIGN PATENT DOCUMENTS

| | | |
|---|---|---|
| WO | WO 92/19244 A2 | 11/1992 |
| WO | WO 97/32572 A2 | 9/1997 |
| WO | WO 97/44013 A1 | 11/1997 |
| WO | WO 98/31346 A1 | 7/1998 |
| WO | WO 99/15154 A1 | 4/1999 |
| WO | WO 99/20253 A1 | 4/1999 |
| WO | WO 99/66903 A2 | 12/1999 |

OTHER PUBLICATIONS

Avis et al., *Pharmaceutical Dosage Forms: Parenteral Medications*; Marcel Dekker, New York, NY; 1993. Cover page, title page and table of contents. 13 pgs.

Bach, *Monoclonal Antibodies and Peptide Therapy in Autoimmune Diseases*, Marcel Dekker, New York, NY; 1993. Cover page, title page and table of contents. 4 pgs.

Baert et al., "Influence of Immunogenicity on the Long-Term Efficacy of Infliximab in Crohn's Disease," *New Eng J Med*, Feb. 13, 2003;348(7):601-608.

Beniaminovitz et al., "Prevention of Rejection in Cardiac Translation by Blockade of the Interleukin-2 Receptor with a Monoclonal Antibody," *New Eng J. Med*, Mar. 2, 2000;342(9):613-619.

Binz et al., "Engineering novel binding proteins from nonimmunoglobulin domains" *Nature Biotechnology*, Oct. 2005; 10: 1257-1268.

(Continued)

*Primary Examiner* — Jennifer Pitrak McDonald
*Assistant Examiner* — Tara L Martinez
(74) *Attorney, Agent, or Firm* — Mueting, Raasch & Gebhardt, PA

(57) ABSTRACT

This disclosure describes non-naturally occurring protein scaffolds and methods of making and using the protein scaffolds. In one aspect, therefore, this disclosure describes a non-naturally occurring protein scaffold that includes a plurality of structural domains and a plurality of loop regions that include an amino acid sequence that varies from a naturally-occurring loop region by at least one amino acid deletion, substitution, or addition. Generally, the structural domain or domains can include at least one β structure and/or at least one α helix.

9 Claims, 23 Drawing Sheets

Specification includes a Sequence Listing.

(56) References Cited

OTHER PUBLICATIONS

Buchwald et al., "Long-term, continuous intravenous heparin administration by an implantable infusion pump in ambulatory patients with recurrent venous thrombosis," *Surgery*, Oct. 1980; 88(4):507-516.
Camara et al., "T7 phage protein Gp2 inhibits the *Escherichia coli* RNA polymerase by antagonizing stable DNA strand separation near the transcription start site," *Proc Natl Acad Sci USA*, Feb. 2, 2010;107(5):2247-2252.
Deere et al., "Flow cytometry and cell sorting for yeast viability assessment and cell selection" *Yeast*, Jan. 1998; 14(2): 147-160.
Ederth et al., "RNA: Structure Metabolism and Catalysis," *J Biol Chem*, Oct. 4, 2002;277(40):37456-37463.
Epstein et al., "Biological activity of liposome-encapsulated murine interferon γ is mediated by a cell membrane receptor," *Proc Natl Acad Sci USA*, Jun. 1, 1985;82(11):3688-3692.
Fraczkiewicz et al., "Exact and Efficient Analytical Calculation of the Accessible Surface Areas and Their Gradients for Macromolecules," *J Comput Chem*, Feb. 1998;19:319-333.
Gai et al., "Yeast Surface Display for Protein Engineering and Characterization," *Curr Opion Struct Biol*, 2007;17:467-473.
Gennaro, *Remington: The Science and Practice of Pharmacy*, Lippincott, Williams, and Wilkins, New York, NY; 2000. Cover page, title page and table of contents. 4 pgs.
Ghosh et al., "Natalizumab for Active Crohn's Disease," *New Eng J Med*, Jan. 2, 2003;348(1):24-32.
Goodson, in *Medical Applications of Controlled Release*, supra, vol. 2, pp. 115-138, 1984; 115-138.
Hackel et al., "Stability and CDR Composition Biases Enrich Binder Functionality Landscapes," *J Mol Biol*, 2010;401:84-96.
Hackel et al., "The full amino acid repertoire is superior to serine/tyrosine for selection of high affinity immunoglobulin G binders from the fibronectin scaffold," *Protein Eng Des Sel*, Apr. 2010;23(4):211-219.
Hackel et al. "Picomolar Affinity Fibronectin Domains Engineered Utilizing Loop Length Diversity, Recursive Mutagenesis, and Loop Shuffling" *Journal of Molecular Biology*, Sep. 19, 2008; 381(5): 1238-1252.
Hackel et al. "Use of $^{64}$Cu-labeled Fibronectin Domain with EGFR-Overexpressing Tumor Xenograft: Molecular Imaging" *Radiology*, Apr. 2012; 263(1): 179-188.
Hackel and Wittrup, "Yeast Surface Display in Protein Engineering and Analysis" *Protein Engineering Handbook—Volume 1 and 2*. Lutz and Bornscheuer (Ed); Wiley-VCH Verlag GmbH & Co., Weinheim Germany;2008;621-648.
Hardman et al., *Goodman and Gilman's The Pharmacological Basis of Therapeutics*, McGraw-Hill: New York, NY; 2001. Cover page, title page and table of contents. 10 pgs.
Herold et al., "Anti-CD3 Monoclonal Antibody in New-Onset Type 1 Diabetes Mellitus," *New Engl J Med*, May 30, 2002;346(22):1692-1698.
Holec, "Engineered High Affinity IGF1R Imaging Agents from the Novel WNM Protein Scaffold," *A Presentation Retrieved from the University of Minnesota Digital Conservancy*, Jun. 13, 2013. http://purl.umn.edu/151535, abstract.
Howard et al., "Intracerebral drug delivery in rats with lesion-induced memory deficits," *J Neurosurg*, Jul. 1989;71(1):105-112.
Hwang et al., "Hepatic uptake and degradation of unilamellar sphingomyelin/cholesterol liposomes: A kinetic study," *Proc Nat Acad Sci USA*, Jul. 15, 1980;77(7):4030-4034.
International Search Report and Written Opinion for PCT/US2014/063441, issued by the United States of American in its capacity as the International Search Authority; dated Jan. 26, 2015; 11 pgs.
International Preliminary Report on Patentabilty for PCT/US2014/063441, issued by the International Bureau of WIPO dated May 12, 2016; 8 pgs.

Kresina, *Monoclonal Antibodies, Cytokines and Arthritis*, Marcel Dekker, New York, NY; 1993. Cover page, title page and table of contents. 5 pgs.
Kruziki et al., "Engineering Picomolar Affinity into a Rationally Identified 5 Kda Scaffold for Tumor Targeting," $5^{th}$ *ICBE—International Conference on Biomolecular Engineering—ICBE 2015*; p. 71-72[online]. Presented on Jan. 14, 2015, Lost Pines, TX [retrieved on Jan. 9, 2017]. Retrieved from the Internet:<URL: https://experts.umn.edu/en/publications/engineering-picomolar-affinity-into-a-rationally-identified-5-kda>; 4 pgs.
Langer and Wise (eds), *Medical Applications of Controlled Release Volume II Applications and Evaluation*, Langer and Wise (eds.), CRC Pres., Boca Raton, Fla., 1974; Cover page, title page and table of contents. 4 pgs.
Langer et al., "Biocompatibility of polymeric delivery systems for macromolecules," *J Biomed Mater Res*, Mar. 1981;15(2):267-277.
Langer et al., "Controlled release of macromolecules," *Chem Tech*, 1982;12:98-105.
Langer and Pepas, "Chemical and Physical Structure of Polymers as Carriers for Controlled Release of Bioactive Agents: A Review," *J Macromol Sci Rev Macromol Chem*, 1983;23(1):61.
Levy et al., "Inhibition of calcification of bioprosthetic heart valves by local controlled-release diphosphonate," *Science*, Apr. 12, 1985;228(4696):190-192.
Lieberman et al., *Pharmaceutical Dosage Forms: Tablets*, Marcel Dekker: New York, NY; 1990. Cover page, title page and table of contents. 12 pgs.
Lieberman et al., *Pharmaceutical Dosage Forms: Disperse Systems*, Marcel Dekker: New York, NY; 1990. Cover page, title page and table of contents. 12 pgs.
Lipsky et al., "Infliximab and Methotrexate in the Treatment of Rhjeumatoid Arthritis," *New Eng J Med*, Nov. 30, 2000;343(22):1594-1602.
Lipovsek et al., "Evolution of an Interloop Disulfide Bond in High-Affinity Antibody Mimics Based on Fibronectin Type III Domain and Selected by Yeast Surface Display: Molecular Convergence with Single-Domain Camelid and Shark Antibodies," *J Mol Biol*, 2007;368:1024-1041.
Liu et al., "Randomised, double blind, placebo controlled study of interferon β-1a in relapsing-remitting multiple sclerosis analysed by area under disability/time curves," *J Neurol Neurosurg Psych*, Oct. 1999;67(4):451-456.
Miao et al., "Protein scaffold-based molecular probes for cancer molecular imaging" *Amino Acids*, Nov. 2011;41(5):1037-1047 (Epub Feb. 21, 2010).
Milgrim et al., "Treatment of Allergic Asthma with Monoclonal Anti-IgE Antibody," *New Engl J Med*, Dec. 23, 1999;341(26):1966-1973.
Orlova et al., "Tumor Imaging Using a Picomolar Affinity HER2 Binding Affibody Molecule" *Cancer Research*, 2006;66: 4339-4448.
Portielji et al., "IL-12: a promising adjuvant for cancer vaccination," *Cancer Immunol Immunother*, Mar. 2003;52(3):133-144.
Remington's Pharmaceutical Sciences and Introduction to Pharmaceutical Dosage Forms, 19th ed., Mack Pub. Co., Easton, Pa., 1995; Cover page, title page and table of contents.
Saudek et al., "A Preliminary Trial of the Programmable Implantable Medication System for Insulin Delivery," *N Eng J Med*, Aug. 31, 1989;321(9):574.
Sefton, "Implantable Pumps," CRC Crit. Ref Biomed. Eng., 1987; 14(3): 41 pgs.
Sheppard et al., "Inhibition of *Escherichia coli* RNAp by T7 Gp2 protein: Role of Negatively Charged Strip of Amino Acid Residues in Gp2," *J Mol Biol*, Oct. 7, 2011;412(5):832-841.
Sidman et al., "Controlled release of macromolecules and pharmaceuticals from synthetic polypeptides based on glutamic acid," *Biopolymers*, Jan. 1983 22:547-556.
Slamon et al., "Use of Chemotherapy plus a Monoclonal Antibody agains HER2 for Metastatic Breast Cancer that Overexpresses HER2," *New Eng J. Med*, Mar. 15, 2001;344(11):783-792.
Smolen and Ball—Controlled Drug Bioavailability, Drug Product Design and Performance, Smolen and Ball (eds.), Wiley, New York (1984).

(56) References Cited

OTHER PUBLICATIONS

Thompson et al., "An improved protocol for the preparation of yeast cells for transformation by electroporation" *Yeast*, 1998;14(6):565-571.
Weiner and Kotkoskie, *Excipient Toxicity and Safety*, Marcel Dekker, Inc.: New York, NY; 2000. Cover page, title page and table of contents. [Optional: ___ pgs (indicates number of pages being submitted—not length of book).].
Yang et al., "A Randomized Trial of Bevacizumab, an Anti-Vascular Endothelial Growth Factor Antibody, for Metastatic Renal Cancer," *New Engl J Med*, Jul. 2003;349(5):427-434.
Yeung and Hackel, "Quantitative Screening of Yeast Surface-Displayed Polypeptide Libraries by Magnetic Bead Capture" *Biotechnology Progress*, 2008;18(2): 212-220.
Yin et al., "Eris: an automated estimator of protein stability," *Nature Methods*, 2007;4:466-467.

\* cited by examiner

Fig. 4A
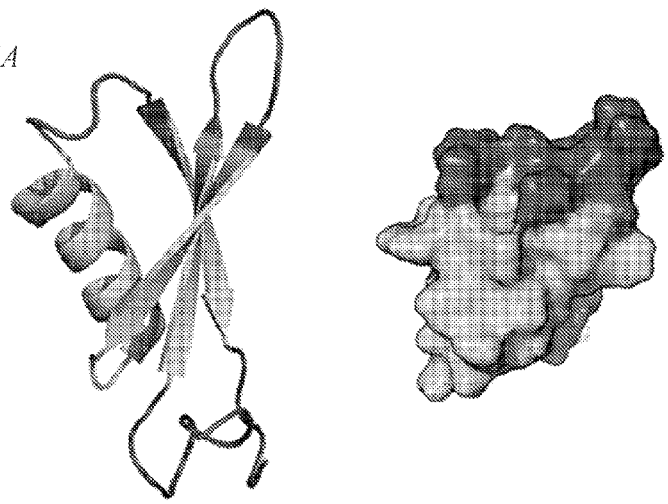
Fig. 4B
1-33  MSNVNTGSLSVDNKKFWATVESS--EHSFEVPVYA
34-64 ETLDEALELAEWQYVPA--GFEVTRVRPCVAPK
Fig. 4C
Fig. 4D
KFWATVess--ehsFEVPIYAETLDEALELAEWQYvpa--gfeVTRVRP
KFWATVXXXXXXXXFEVPVYAETLDEALELAEWQYXXXXXXXXVTRVRP

| Gp2 Mutant | Frame | Loop 1 | Loop 2 | $K_{D, yeast}$ (nM) | $K_{D, soluble}$ (nM) | $T_m$ (°C) |
|---|---|---|---|---|---|---|
| Wild Type | - | ESSEHS | VPAGFE | - | - | 67 ± 1 |
| Goat IgG 2.2.1 | E45V, Q47R | YDYDADYY | YSNHSDYL | 0.2 ± 0.1 | 0.4 ± 0.3 | 70 ± 4 |
| Lysozyme A0.3.2 | - | FSYGNL | SGAYEY | ~1550 | n.d. | n.d. |
| Rabbit IgG 3.2.3 | E45F, W46G | HSVHGY | GNALGY | 1.5 ± 0.6 | 1.0 ± 0.5 | 80 ± 1 |

Fig. 7

| Clone | Strain | Yield (mg/L) |
|---|---|---|
| Wild-type | BL21 | 0 |
| Wild-type | JE1(DE3) | 0.7 |
| GaG 2.2.1 | BL21 | 0.2 |
| GaR 3.2.3 | BL21 | 2.2 |
| GaE 2.3.3h | BL21 | 2.5 |

Gp2 / cell (c-myc signal)

PROTEIN SCAFFOLDS AND METHODS OF USE

CROSS-REFERENCE TO RELATED APPLICATION

This application is the § 371 U.S. National Stage of International Application No. PCT/US2014/063441, filed 31 Oct. 2014, which claims priority to U.S. Provisional Patent Application No. 61/898,723, filed Nov. 1, 2013, and U.S. Provisional Patent Application No. 62/017,470, filed Jun. 26, 2014, each of which is incorporated herein by reference in its entirety.

SEQUENCE LISTING

This application contains a Sequence Listing electronically submitted to the United States Patent and Trademark Office via EFS-Web as an ASCII text file entitled "110-4400201_SequenceListing_ST25.txt" having a size of 33 KB. Due to the electronic filing of the Sequence Listing, the electronically submitted Sequence Listing serves as both the paper copy required by 37 CFR § 1.821(c) and the CRF required by § 1.821(e). The information contained in the Sequence Listing is incorporated by reference herein.

SUMMARY

This disclosure describes non-naturally occurring protein scaffolds and methods of making and using the protein scaffolds. In one aspect, therefore, this disclosure describes a non-naturally occurring protein scaffold that includes a plurality of structural domains and a plurality of loop regions that include an amino acid sequence that varies from a naturally-occurring loop region by at least one amino acid deletion, substitution, or addition. Generally, the structural domain or domains can include at least one β structure or at least one α helix.

In some embodiments, the protein scaffold can include an α helix and two β structures. In some of these embodiments, the α helix and the β structure are, or are derived from corresponding portions of, gene protein 2 (Gp2) of T7 phage.

In some embodiments, the protein scaffold can include a loop region that varies from a naturally-occurring loop region of Gp2 of T7 phage.

In some embodiments, the protein scaffold can include the structural domains of the amino acid sequence of SEQ ID NO:129. In some of these embodiments, the protein scaffold can include the amino acid sequence of SEQ ID NO:129.

In another aspect, this disclosure describes pharmaceutical compositions that include a protein scaffold as described herein. Thus, this disclosure also provides methods that include administering a pharmaceutical composition to a subject in need of treatment for a condition treatable by the pharmaceutical composition.

In another aspect, this disclosure describes a diagnostic composition that includes a protein scaffold as described herein. In some embodiments, the protein scaffold in a detection composition can include a detectable marker.

In another aspect, this disclosure provides a method for detecting a target molecule. Generally, the method includes providing a protein scaffold as described herein that specifically binds the target molecule, contacting the protein scaffold with a sample that includes the target molecule, and detecting at least one protein scaffold:target molecule complex.

In another aspect, this disclosure provides a method of preparing a protein scaffold library. Generally, the method includes providing a plurality of protein scaffolds, contacting at least a portion of the protein scaffolds with a target, thereby allowing formation of a plurality of protein scaffold:target complexes, separating at least a portion of the protein scaffold:target complexes from unbound protein scaffolds, and causing release of the protein scaffold from at least a portion of the separated protein scaffold:target complexes.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 4. (A) Ribbon diagram of Gp2 structure. (B) Full Gp2 amino acid sequence, SEQ ID NO:129. The diversified amino acids are underlined. The I31V (boldface) mutation was added based on its prevalence in homologous protein sequences (sequence logo). The N-terminal and C-terminal tails highlighted were removed to create the tGp2 scaffold. (C) Natural sequence frequency 'sequence logo' indicating amino acid frequency of Gp2 homologs (SEQ ID NO:130). Site 31 is outlined. (D) Truncated Gp2 library design where X in SEQ ID NO:132 (bottom) indicates a diversified amino acid or amino acid deletion relative to SEQ ID NO:131 (top). One to eight amino acids can occupy either XXXXXXXX region (residues 7-14 and residues 36-43 of SEQ ID NO:132).

FIG. 7. Production titers of various tGp2 clones in *E. coli*. Gp2 clones were produced in the soluble fraction of *E. coli* (BL21 or JE1(DE3)) and purified by metal affinity chromatography. Wild-type Gp2 is not effectively produced in standard BL21, whereas mutant clones are readily produced. Wild-type Gp2 is successfully made in JE1(DE3).

DETAILED DESCRIPTION OF ILLUSTRATIVE EMBODIMENTS

Figure 1:
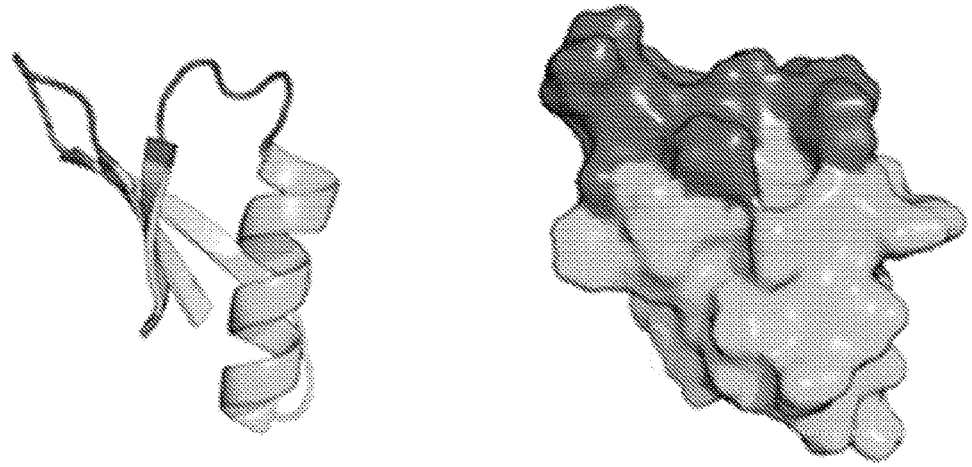
FIG. 1. Illustration of the structure of an exemplary protein scaffold based on truncated gene protein 2 (tGp2).

This disclosure describes molecules that can specifically bind to a target, methods for generating these molecules, and methods of using these molecules. The molecules can have use in a clinical and/or research and discovery setting.

Molecules that recognize certain targets specifically and with high affinity are useful for many clinical (e.g., diagnostic and/or therapeutic) and biotechnology applications. Typically, antibodies have been used for many of these applications, but antibodies have certain properties that may be drawbacks in certain applications. The limitations of antibodies have encouraged investigation toward alternative protein scaffolds that allow one to efficiently generate improved binding molecules. In the context of targeting solid tumors, for example, antibodies—which are typically about 150 kDa for immunoglobulin G (IgG)—can exhibit, due at least in part to their size, poor extravasation from vasculature, poor penetration through tissue, and/or long plasma clearance halftime, which can lead to poor signal-to-noise ratio, especially for diagnostic imaging. Antibodies also can exhibit thermal instability, which can lead to a loss of efficacy as a result of denaturation and/or aggregation. In addition, antibodies are typically made in mammalian cultures because many possess disulfide bonds, glycosylation, and/or multi-domain structures. This intricate structure can interfere with engineering the antibody for a particular application such as, for example, production of protein fusions for bispecific formats. Moreover, the presence of disulfide bonds in antibody molecules often precludes their intracellular use.

As a result of the limitations inherent to antibodies, alternative protein scaffolds have been developed in attempts to address many or all of these shortcomings. This disclosure describes recombinant, non-naturally occurring protein scaffolds capable of binding a compound of interest. In particular, the protein scaffolds described herein may be used to display defined loops that are analogous to the complementarity-determining regions ("CDRs") of an antibody variable region. These loops may be subjected to randomization or restricted evolution to generate the diversity required to build a library of scaffold proteins that, while each scaffold binds to a specific target, the library, collectively, binds to a multitude of target compounds. The protein scaffolds may be assembled into a multispecific scaffold capable of binding different two or more targets. The protein scaffolds described herein can therefore provide functional properties typically associated with antibody molecules. In particular, despite the fact that the scaffold is not an immunoglobulin, its overall folding is similar in relevant respect to that of the variable region of the IgG heavy chain, making it possible for a protein scaffold to display loops in relative orientations analogous to antibody CDRs. Because of this structure, the scaffolds described herein possess ligand binding properties that are similar in nature and affinity to the binding properties of antigen and antibody. Also, loop randomization and shuffling strategies may be employed in vitro that are similar to the process of affinity maturation of antibodies in vivo.

The engineered protein scaffolds described herein are can provide a platform upon which amino acid diversity can be introduced to develop novel function. In some embodiments, a protein scaffold can be efficiently evolvable to bind with the affinity and specificity typical of antibodies, but be more stable and/or exhibit better biodistribution that typically exhibited by antibodies. As a result, the protein scaffold may be useful in a wider range of applications and settings than a corresponding antibody molecule. In some embodiments, a protein scaffold can be efficiently evolved to bind specifically to a target with a desired affinity, which in many applications may be characterized by a nanomolar to picomolar dissociation constant. High affinity and specificity can provide targeted delivery and/or reduce side effects in clinical applications. A scaffold free of disulfide bonds allows for bacterial production in the reducing E. coli cellular environment, intracellular stability in mammals, and/or ease of chemical conjugation. A protein scaffold benefits from retaining the native structure of its structural (a helix and/or β structure) and stability through the numerous possible mutations to the variable loop domains that can confer binding specificity.

The protein scaffolds described herein can serve as a platform for ligand discovery towards a broad range of clinical, scientific, and/or industrial targets. For example, small protein scaffolds can possess permeability and/or distribution properties that make them suitable for, for example, targeting nascent tumors. Scaffolds also can be suitable for targeting atherosclerotic plaque and other biologically distinct vascular states. In other embodiments, scaffolds can be suitable for drug delivery to the central nervous system for treatment and/or diagnosis of neurological disorders or diagnosis of neurobiological status. Scaffolds also can be suitable for delivery to immune cells for immune modulation and/or immune surveillance. As yet another example, scaffolds can be suitable for delivery to stem cells for modulation and/or diagnosis of cellular status.

This disclosure describes a platform for engineering a small (approximately 5 kDa), stable protein scaffold capable of efficient modification to generate target-specific picomolar affinity that can provide for sustained delivery in vivo. As used herein, "specific" and variations thereof refer to having a differential or a non-general affinity, to any degree, for a particular target. We analyzed the secondary structure, stability, phylogenetic sequence diversity, and the accessible surface area and shape of the potential paratope of proteins throughout characterized proteomes to identify candidate scaffolds for engineering molecular recognition. Generally, the scaffold includes a recombinant, non-naturally occurring protein scaffold capable of binding a compound of interest. In particular, the protein scaffolds described herein may be used to display defined loops that are analogous to the complementarity-determining regions ("CDRs") of an antibody variable region. The variability of the loop regions permit generating protein scaffold molecules that can specifically bind to any target of interest. The loops maybe subjected to randomization or restricted evolution to generate sufficient diversity that a library of protein scaffold molecules can include sufficient members that the library, as a whole, can bind to a multitude of targets. Moreover, the scaffold proteins may be assembled into a multispecific scaffold—e.g., a multimeric scaffold—capable of specifically binding two or more different targets.

This disclosure therefore describes recombinant, non-naturally occurring polypeptide scaffolds that include a plurality of β strand domains linked to a plurality of loop regions. The loop regions can possess an amino acid sequence from, or derived from, a naturally occurring amino acid sequence. As used herein, an amino acid sequence "derived from" a naturally occurring amino acid sequence may exhibit one or more amino acid additions, amino acid substitutions, amino acid deletions, and/or post-translational modifications (collectively, "modifications") to confer a desired functionality such as, for example, binding specificity and/or controlled reactability. Thus, one or more of the loop region amino acid sequences vary by deletion, substitution, and/or addition by at least one amino acid from the corresponding loop amino acid sequences of the naturally occurring protein from which it is derived. Moreover, the β strand domains of the protein scaffold can have at least 50% amino acid sequence identity to the amino acid sequence of a corresponding domain of a naturally occurring protein.

In one exemplary embodiment, the scaffold includes 45 amino acids that include an alpha helical domain, two beta strand domains, and two exposed loop domains. The alpha helical domain and the beta structural domains (collectively referred to herein as the scaffold "frame") provide structural stability while the loop domains can be amenable to mutation. Modifying the amino acid sequence in the loop domains permits discovery of new molecular entities with novel binding function while the scaffold frame (i.e., the α helix and β structure) impart structural stability. We diversified twelve amino acids in these two loops using complementarity bias and length diversity to generate a combinatorial library for ligand discovery. Directed evolution was performed using yeast surface display and magnetic and fluorescence selections. Protein scaffold molecules that bound to one of three targets were isolated with affinities as strong as 200 pM. We performed biophysical characterization including circular dichroism and thermal stability. The resulting data establish that the protein scaffold platform can be an effective tool for robust, efficient engineering of small (e.g., 5 kDa), stable ligands.

This disclosure describes, therefore, a technological platform that may be used for designing and producing ligands for diagnostic and/or therapeutic targeting. The protein scaffold platform described herein provides a unique combination of small size, high affinity binding, good stability and/or chemical compatibility. The small size can facilitate physiological distribution. High binding affinity can facilitate retention at the target site. The stability and chemical compatibility facilitate breadth of applications in which the protein scaffold molecules can be used.

The protein scaffold may be any suitable size commensurate with providing desired properties for a particular application. Generally, the protein scaffold can have a minimum length of at least 30 amino acids such as, for example, a minimum length of at least 35 amino acids, at least 36 amino acids, at least 37 amino acids, at least 38 amino acids, at least 39 amino acids, at least 40 amino acids, at least 41 amino acids, at least 42 amino acids, at least 43 amino acids, at least 44 amino acids, at least 45 amino acids, at least 46 amino acids, at least 47 amino acids, at least 48 amino acids, at least 49 amino acids, at least 50 amino acids, at least 51 amino acids, at least 52 amino acids, at least 53 amino acids, at least 54 amino acids, at least 55 amino acids, at least 56 amino acids, at least 57 amino acids, at least 58 amino acids, at least 59 amino acids, or at least 60 amino acids. The protein scaffold can have a maximum length of no more than 65 amino acids such as, for example, no more than 64 amino acids, no more than 63 amino acids, no more than 62 amino acids, no more than 61 amino acids, no more than 60 amino acids, no more than 59 amino acids, no more than 58 amino acids, no more than 57 amino acids, no more than 56 amino acids, no more than 55 amino acids, no more than 54 amino acids, no more than 53 amino acids, no more than 52 amino acids, no more than 51 amino acids, no more than 50 amino acids, no more than 49 amino acids, no more than 48 amino acids, no more than 47 amino acids, no more than 46 amino acids, no more than 45 amino acids, no more than 44 amino acids, no more than 43 amino acids, no more than 42 amino acids, no more than 41 amino acids, or no more than 40 amino acids. In some embodiments, the scaffold may have a length expressed as a range having endpoints defined by any minimum length listed above and any maximum length greater than the minimum length. In various embodiments, the protein scaffold may have a length of, for example, 35 amino acids, 36 amino acids, 37 amino acids, 38 amino acids, 39 amino acids, 40 amino acids, 41 amino acids, 42 amino acids, 43 amino acids, 44 amino acids, 45 amino acids, 46 amino acids, 47 amino acids, 48 amino acids, 49 amino acids, 50 amino acids, 51 amino acids, 52 amino acids, 53 amino acids, 54 amino acids, 55 amino acids, 56 amino acids, 57 amino acids, 58 amino acids, 59 amino acids, 60 amino acids, 61 amino acids, 62 amino acids, 63 amino acids, 64 amino acids, or 65 amino acids.

Generally, the protein scaffold possesses secondary structure that includes structurally stable domains and solvent-accessible, mutation-amenable loops. The structural domains (i.e., the scaffold frame) can include, for example, β structures and/or a structures sufficient to provide structural integrity and stability to the protein scaffold. In one particular embodiment, the protein scaffold can include an α helical domain and two β structural domains.

For example, in some embodiments, the protein scaffold can include a minimum of at least 20% of the amino acids being dedicated to β sheet secondary structure such as, for example, at least 25% β sheet secondary structure, at least 26% β sheet secondary structure, at least 27% β sheet secondary structure, at least 28% β sheet secondary structure, at least 29% β sheet secondary structure, at least 30% β sheet secondary structure, at least 31% β sheet secondary structure, at least 32% β sheet secondary structure, at least 33% β sheet secondary structure, at least 34% β sheet secondary structure, or at least 35% β sheet secondary structure. In some embodiments, the protein scaffold can include a maximum of no more than 40% of the amino acids being dedicated to β sheet secondary structure such as, for example, no more than 39% β sheet secondary structure, no more than 38% β sheet secondary structure, no more than 37% β sheet secondary structure, no more than 36% β sheet secondary structure, no more than 35% β sheet secondary structure, no more than 34% β sheet secondary structure, no more than 33% β sheet secondary structure, no more than 32% β sheet secondary structure, no more than 31% β sheet secondary structure, or no more than 30% β sheet secondary structure. In some embodiments, the extent of β sheet secondary structure can be expressed as a range having endpoints defined by any minimum β sheet secondary structure listed above and any maximum β sheet secondary structure listed above that is greater than the minimum β sheet secondary structure. In various embodiments, the protein scaffold may have 25%, 26%, 27%, 28%, 29%, 30%, 31%, 32%, 33%, 34%, 35%, 36%, 37%, 38%, 39%, or 40% of its amino acids devoted to β sheet secondary structure. As used herein, when referring to a percentage of amino acids devoted to β sheet secondary structure, the percentage values reflect percentages rounded to the nearest whole integer value. Thus, for example, percentages of 34.50%, 34.62%, 35.31%, and 35.49% are included in 35%.

The scaffold frame generally corresponds to amino acids 15-20, 27-47, and 54-59 of wild-type Gp2 (SEQ ID NO:129). The scaffold frame can exhibit, however, one or more amino acid modifications—e.g., one or more amino acid additions, amino acid substitutions, amino acid deletions-relative to the native Gp2 amino acids of the scaffold frame (amino acids 15-20, 27-47, and 54-59 of SEQ ID NO:129). Exemplary scaffold frame modifications are listed in Table 1. Thus, the scaffold frame can have an amino acid identity of at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence relative to the native Gp2 amino acid sequence of the scaffold frame. In some embodiments, an amino acid substitution in the scaffold frame can involve a conservative amino acid substitution. A conservative substitution may be selected from other members of the class to which the amino acid belongs. For example, it is well-known in the art of protein biochemistry that an amino acid belonging to a grouping of amino acids having a particular size or characteristic (such as charge, hydrophobicity and hydrophilicity) can be substituted for another amino acid without altering the activity of a protein. For example, nonpolar (hydrophobic) amino acids include alanine, leucine, isoleucine, valine, proline, phenylalanine, tryptophan, and tyrosine. Polar neutral amino acids include glycine, serine, threonine, cysteine, tyrosine, asparagine, and glutamine. The positively charged (basic) amino acids include arginine, lysine, and histidine. The negatively charged (acidic) amino acids include aspartic acid and glutamic acid. Conservative substitutions include, for example, Lys for Arg and vice versa to maintain a positive charge; Glu for Asp and vice versa to maintain a negative charge; Ser for Thr so that a free —OH is maintained; and Gln for Asn to maintain a free —NH$_2$.

Figure 2A:
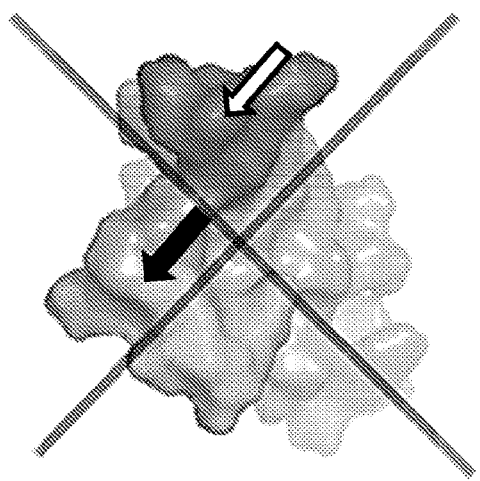
FIG. 2. Protein (A) was not selected while protein (B) was. The light grey area indicated by the filled arrow represents the surface of the protein while the dark grey area indicated with the open arrow represents that of the loops. The loops are clearly disjointed in protein (A).
Figure 2B:
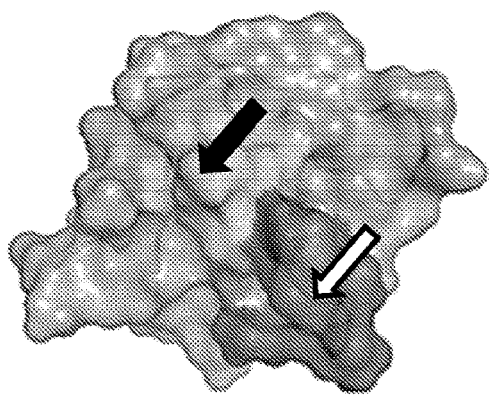
Figure 3:
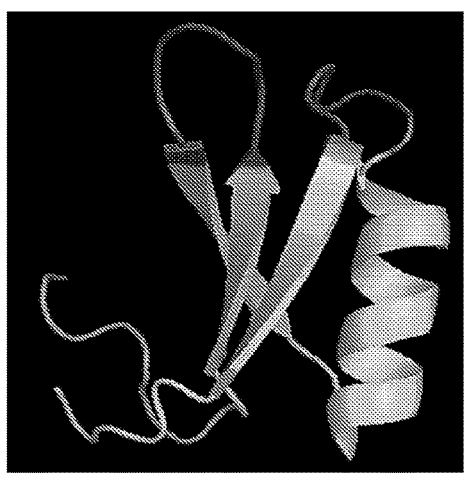
FIG. 3. tGp2 is shown (SEQ ID NO:128). The light grey represents the secondary structures of the protein while the dark grey represents the loops.
Figure 3:
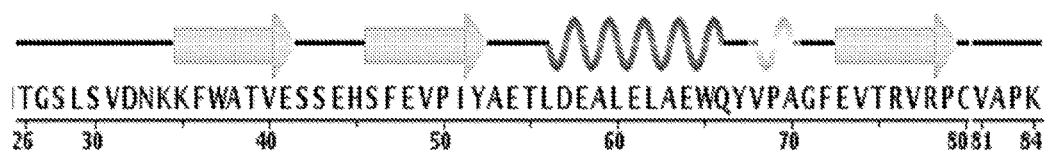

The solvent-accessible, mutation-amenable domains should be in sufficient proximity to one another to form a combined binding domain (see, e.g., FIG. 2B). The combined binding domain formed by the solvent-accessible, mutation-amenable loops will have a surface area. In some embodiments, the protein scaffold may be designed to increase the binding domain surface area, thereby increasing the binding area accessible to a target and, consequently, increasing the likelihood that the particular protein scaffold will bind the target.

The surface area may be modeled by any suitable method. One method involves analysis using molecular visualization software such as, for example, PyMOL. Such software allows one to highlight the surface of the structural domain(s) of the protein scaffold with one color, while highlighting the surface of the loop region with a different color. FIG. 2 shows a comparison of molecular visualization between two potential protein scaffolds. FIG. 2A shows a molecular structure in which the loop domains are separated and fail to form a combined binding domain. In contrast, FIG. 2B shows a molecular structure in which the loop domains form a combined binding domain. The surface are also may be modeled using surface area-calculating software such as, for example, GetArea (Fraczkiewicz et al. 1998. *Journal of Computational Chemistry* 19:319-333.).

In some embodiments, the protein scaffold may be based on a protein with limited disulfide bonds and, in some cases, may include no disulfide bonds. Disulfide bonds can become reduced in an intracellular environment and may require proper oxidation during synthesis or microbial production. Antibody fragments and several other binding proteins often possess disulfide bonds. When disulfide bonds are reduced in the intracellular milieu, binding proteins that rely on disulfide bonds may exhibit limited stability and/or poor intracellular activity.

Generally, the stability offered by the structurally stable domains can support the functionality of the loop domains. Since amino acid modifications are made in the variable, mutation-amenable loops, the structurally stable domains can be designed so that modifications to the loop do not significantly increase the extent and/or likelihood that the modified protein scaffold denatures.

The stability of a protein scaffold may be assessed using software such as, for example ERIS (University of North Carolina; Yin et al. 2007. *Nature Methods* 4:466-467). The software can provide a ΔΔG value in kcal/mole for a particular amino acid sequence, with negative values of ΔΔG reflecting amino acid sequences of more stable protein scaffolds.

To investigate an exemplary protein scaffold, we selected gene protein 2 (Gp2) from T7 phage as the basis for the protein scaffold because of its size, conformational stability upon mutation, lack of disulfides, and available binding surface. Gp2 is an *E. coli* RNA polymerase inhibitor from T7 phage. Wild-type Gp2 contains one alpha helix and three beta strands and includes 64 amino acids. Coils at the N-terminus (14 amino acids) and the C-terminus (5 amino acids) of the wild-type Gp2 were removed, resulting in tGp2: a 5.2 kDa, 45 amino acid protein (FIG. 1, SEQ ID NO:1). The smaller size of tGp2 compared to the wild-type Gp2 may confer favorable biodistribution, plasma clearance, and/or tumor penetration properties. Two loops, illustrated in FIG. 1 and indicated by underlining in SEQ ID NO:129, were identified as the binding surface, based on their size, exposed area, and proximity.

A library, containing approximately $4 \times 10^8$ tGp2 molecules (based on the number of yeast transformants) was constructed by randomizing six amino acids from each loop based on the CDR-inspired library design (Hackel et al. 2010. *J Mol Biol* 401:84-96), and allowing loop length diversity of 6, 7, or 8 amino acids in each loop (FIG. 4). Hemagglutinin (HA) and c-myc epitope tags placed upstream and downstream of the tGp2 coding region, respectively, allowed for differentiation through flow cytometry of yeast that lost the plasmid (HA$^-$/c-myc), yeast carrying a plasmid with incomplete tGp2 (HA$^+$/c-myc), and yeast expressing full length tGp2 (HA$^+$/c-myc A quality control check by flow cytometry indicated that 44% of yeast harboring plasmid expressed full length tGp2. This was supported through sequencing of 10 tGp2 coding regions, resulting in four full length tGp2 coding regions, one tGp2 containing a stop codon in the diversified loop and five frame shifted coding regions. Therefore, the actual size of the library was $1.8 \times 10^8$ unique, full length tGp2 proteins. Amino acid diversity matched the designed distribution.

Lysozyme, immunoglobulin G (IgG) from rabbit, and IgG from goat were chosen as the first targets for evaluating the binding potential of the tGp2 scaffold. These three proteins were selected because they provided differences of size, differences in shape as, and/or were readily available as purified proteins from commercial sources.

During each evolutionary round, the tGp2 library underwent two selection sorts—on magnetic beads and through fluorescence activated cell sorting (FACS)—and one sort to ensure the tGp2 was full length. Sorted tGp2 sequences were mutated through parallel error-prone PCR reactions targeting the loops or the entire coding region and transformed into yeast with loop shuffling driven by homologous recombination (Hackel et al. 2010. *J Mol Biol* 401:84-96). Two to four rounds of selection and mutation were carried out for each target in order to isolate binders with low nanomolar to picomolar affinity.

Figures 5A, 5B:
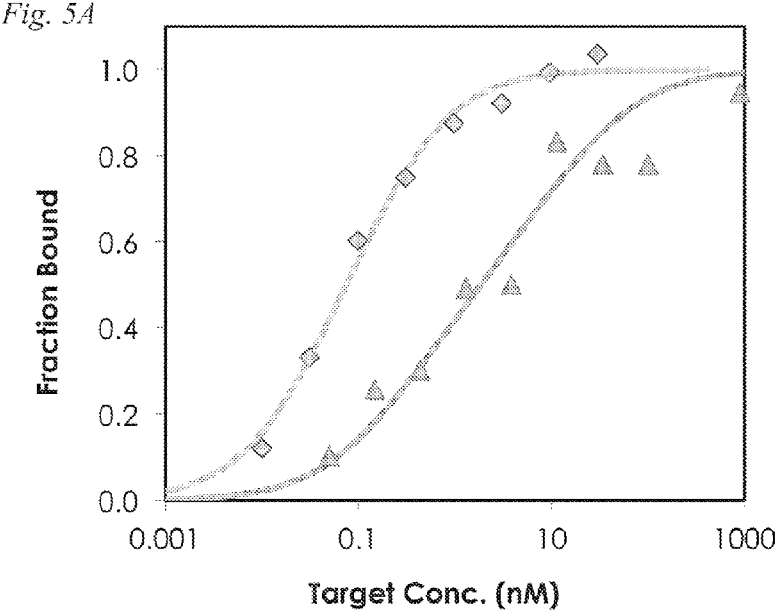
FIG. 5. (A) Affinity titration data for various protein scaffold clones against target proteins lysozyme, rabbit IgG, and goat IgG. ◇: Goat IgG 2.2.1; ▲: Rabbit IgG 3.2.3. (B) IgG-binding mutants have high affinity. Equilibrium binding dissociation constant ($K_D$) agrees on the surface of yeast and as a soluble protein. Mutants have higher midpoint of thermal denaturation ($T_m$) than tGp2 wild type as measured by circular dichroism. n.d.—not determined. The sequences of the diversified loops are shown. Specifically, the Gp2 clone sequences shown are wild type loop 1 (SEQ ID NO:133) and loop 2 (SEQ ID NO:134), goat IgG 2.2.1 loop 1 (SEQ ID NO:16) and loop 2 (SEQ ID NO:17), lysozyme A0.3.2 loop 1 (SEQ ID NO:116) and loop 2 (SEQ ID NO:117), and rabbit IgG 3.2.3 loop 1 (SEQ ID NO:44) and loop 2 (SEQ ID NO:45). Amino acid modifications in the structural domains are shown with reference to the Gp2 sequence shown in FIG. 4(B).

Single clones were isolated at the end of rounds where strong binding was detectable by FACS. Target affinity on the surface of yeast was determined by concentration titration (FIG. 5). Affinities on the surface of yeast typically match soluble affinities (Gai et al. 2007. *Curr. Opin. Struct. Biol.* 17:467-473). The goat IgG binding population contained one dominant protein group that had affinities as strong as 200 pM after one mutagenic cycle. An exemplary clone from this group, containing the variable loop amino acid sequences and the scaffold frame mutations shown in FIG. 5B, is variously referred to herein as Goat IgG 2.2.1 (e.g., FIG. 5B), gIgG 2.2.1 (e.g., FIG. 6), and GaG 2.2.1 (e.g., FIG. 7). The rabbit IgG binding population contained a family of low nanomolar affinity binders at the end of the third mutagenic cycle, which increased to 1 nM after another round of affinity maturation. An exemplary clone from this group, containing the variable loop amino acid sequences and the scaffold frame mutations shown in FIG. 5B, is variously referred to herein as Rabbit IgG 3.2.3 (e.g., FIG. 5B), rIgG 3.2.3 (e.g., FIG. 6), and GaR 3.2.3 (e.g., FIG. 7). A single dominant clone group was isolated for lysozyme binders after the second round of mutagenesis. An exemplary clone from this group, containing the variable loop amino acid sequences shown in FIG. 5B, is identified as Lysozyme A0.3.2. tGp2 clones isolated in subsequent rounds showed point mutations but no significant increase in binding affinity.

Figure 6:
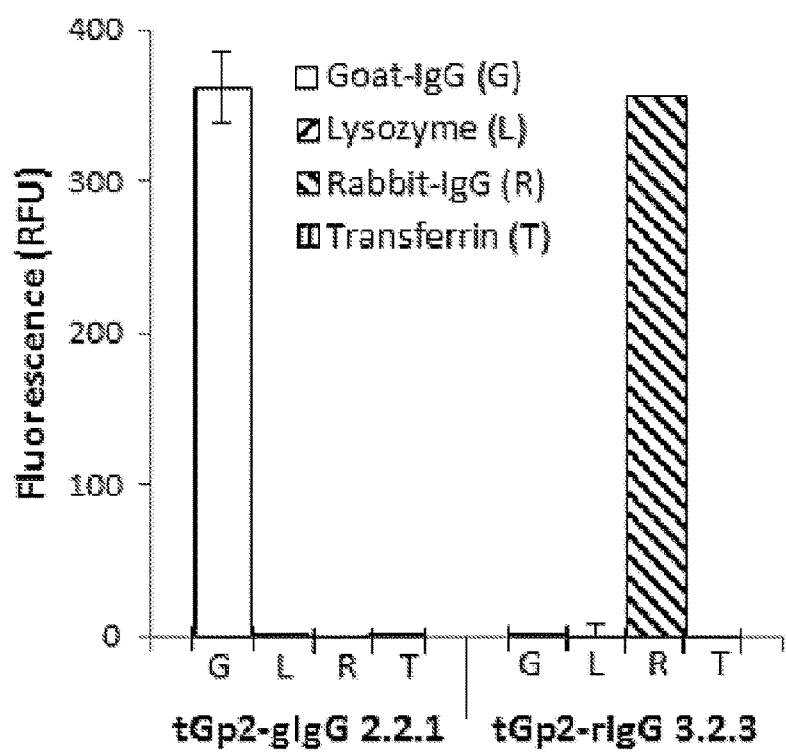
FIG. 6. Binding specificity data for various protein scaffold clones. Fluorescence of tGp2 displaying yeast clones, labeled with multiple biotinylated proteins at 50 nM. Mutants display strong labeling with proteins for which they were selected and matured, compared to negative controls. Error bars represent biological triplicates.

To examine target specificity, two of the strongest binders of each target were labeled with four proteins at 50 nM. All tGp2 proteins show strong fluorescence signal when labeled with the target protein for which they were selected and matured, while showing fluorescence only slightly above background signal for the three other proteins (FIG. 6). Four depletion sorts were performed per round, consisting of two sorts to bare streptavidin coated beads and two sorts to non-target protein coated beads. This sorting process enabled only tGp2 binders to the protein of interest to be carried through the affinity maturation process.

Wild type tGp2 could not be produced at detectable levels in *E. coli* BL21(DE3), perhaps due, at least in part, to the protein's native RNA polymerase inhibition function. However, mutated clones were able to be produced, perhaps due, at least in part, to mutation of many of the positively charged residues on tGp2 that are normally involved in interacting with DNA during transcription inhibition (Camara et al. 2010. *Proc. Natl. Acad. Sci. U.S.A.* 107:2247-2252). Production titer was dependent on the individual tGp2 clone, but ranged between 0.2 mg/L and 2.2 mg/L. (FIG. 7).

Figure 8A:
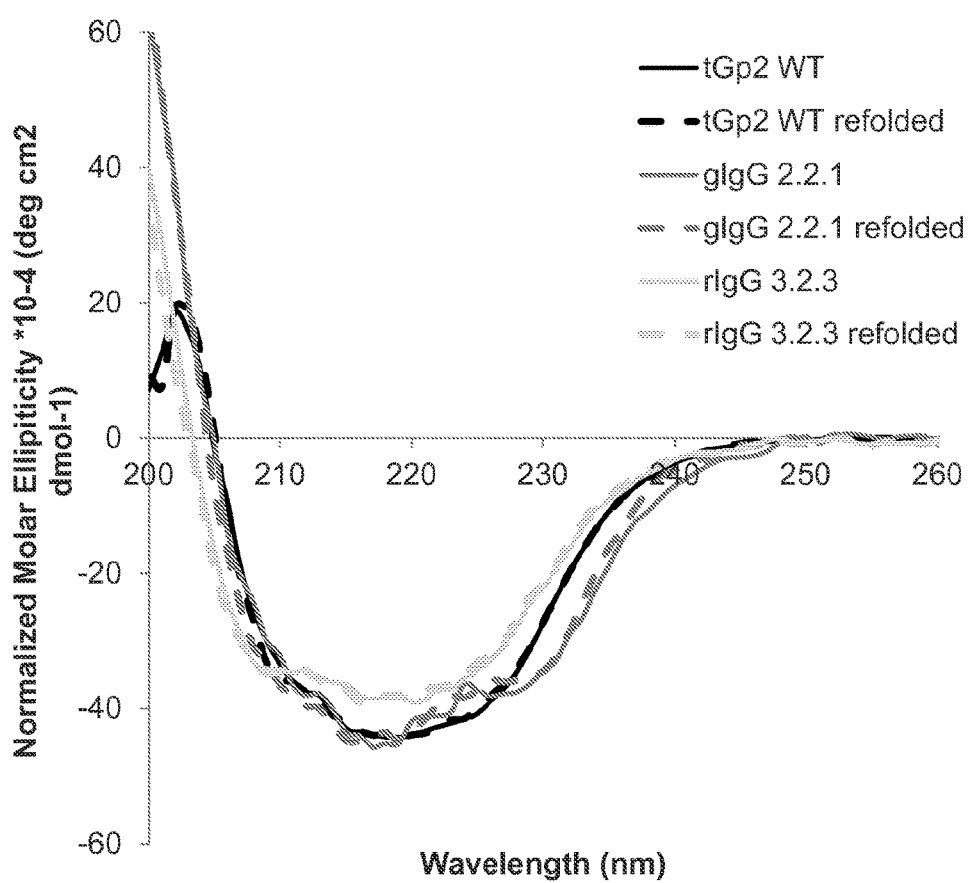
FIG. 8. Circular dichroism data for wild-type truncated Gp2 (tGp2 WT) and representative tGp2 clones tGp2-gIgG 2.2.1, tGp2-rIgG 3.2.3, and tGp2-EGFR. Circular dichroism wavelength scan, verifying similar secondary structure for tGp2 WT and binding mutants. Dotted lines are cooled after thermal denaturation, showing refolding.
Figure 8B:
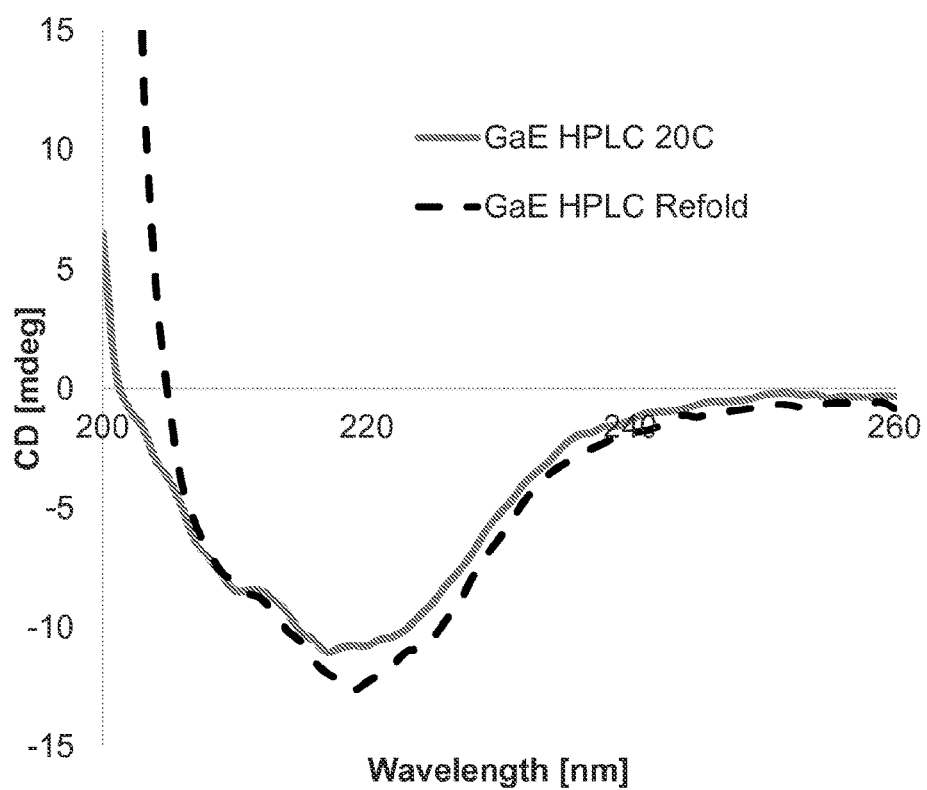
Figure 9A:
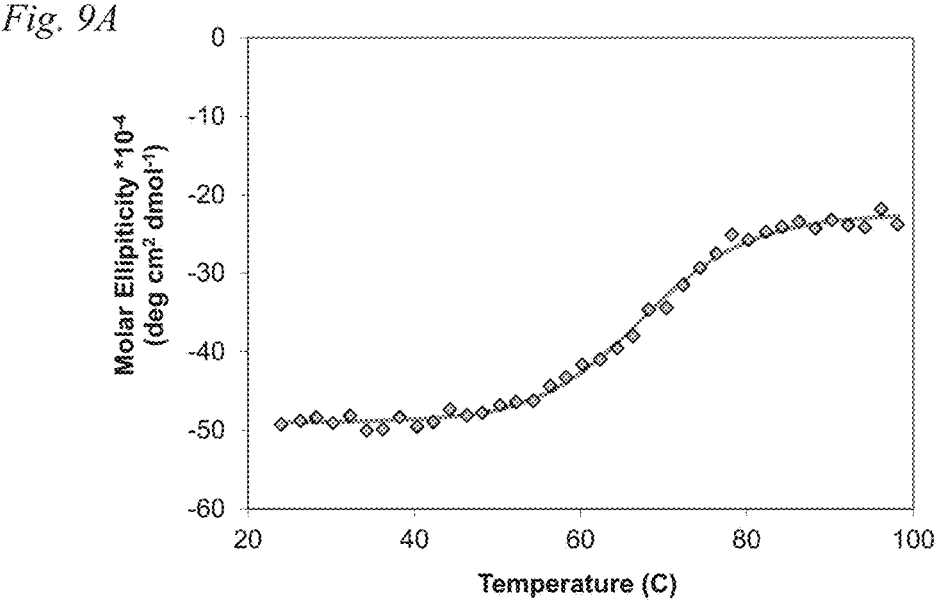
FIG. 9. Circular dichroism melting temperature data for (A) wild type truncated Gp2 (67° C.); (B) clone tGp2-gIgG 2.2.1 (70° C.); (C) tGp2-rIgG 3.2.3 (80° C.); and (D) tGp2-EGFR (81° C.).
Figure 9B:
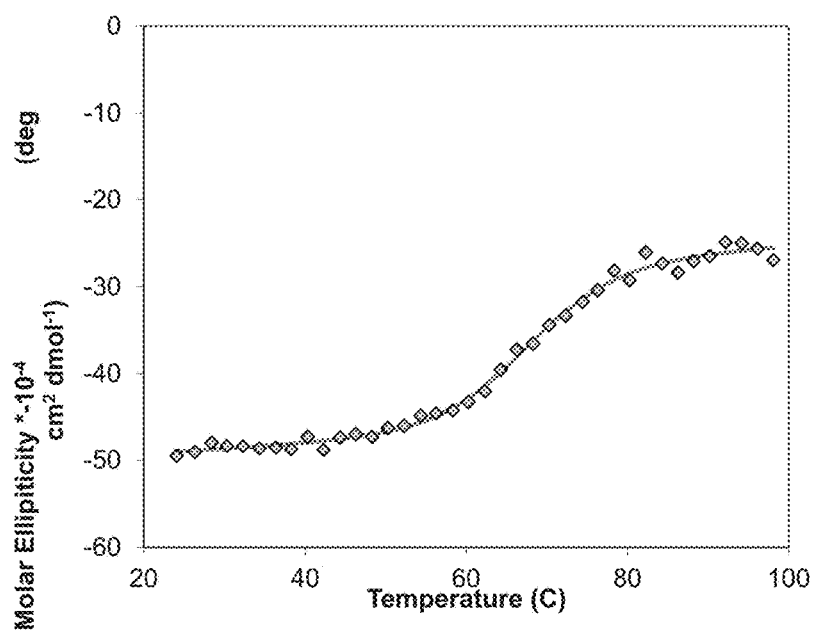
Figure 9C:
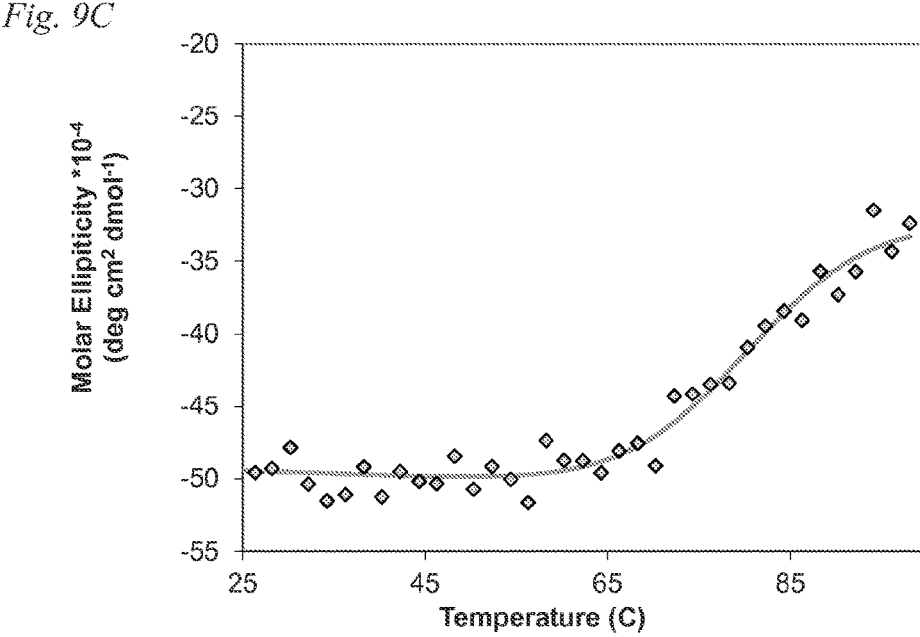
Figure 9D:
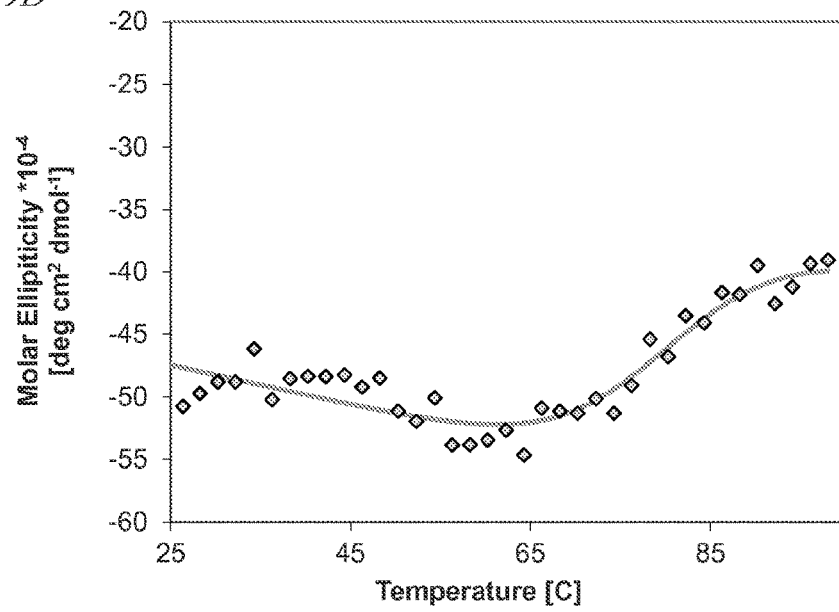

In order to determine how the secondary structure of a tGp2 protein scaffold may change after tGp2 has been affinity matured, we performed circular dichroism analyses on the top binder for each target. The ellipticity spectra of the binding tGp2 proteins deviates only slightly from the wild-type tGp2, suggesting that the percentages of secondary structure remains relatively unchanged after multiple mutations in the backbone and entirely new loop regions (FIG. 8). Thermal melting of each protein was carried out in order to determine the melting temperature, based on the amount of loss of secondary structure at 218 nm over the temperature range (FIG. 9). Interestingly, tGp2 wild type had the lowest melting temperature of all clones examined at 67° C., with the melting temperature increasing by an average of 7° C. for the mutated clones.

Figure 10A:
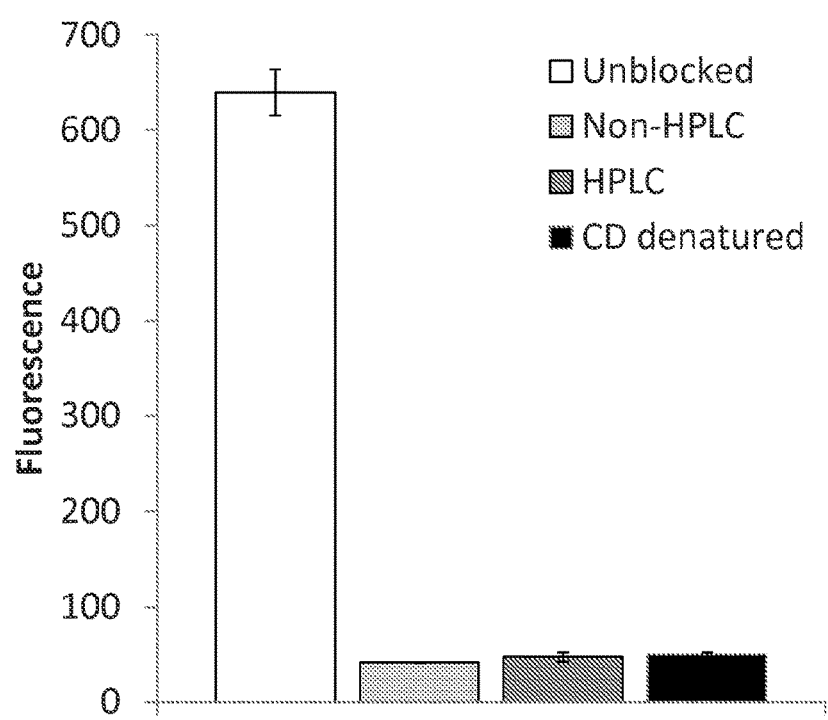
FIG. 10. (A) Soluble protein binding data for a representative tGp2 clone (Gag 2.2.1); (B) and (C): Competition of tGp2-rIgG$_{3.2.3}$ (B) and tGp2-gIgG 2.2.1 (C) where the target was blocked by soluble tGp2 and then used to label tGp2 displayed on yeast.
Figure 10B:
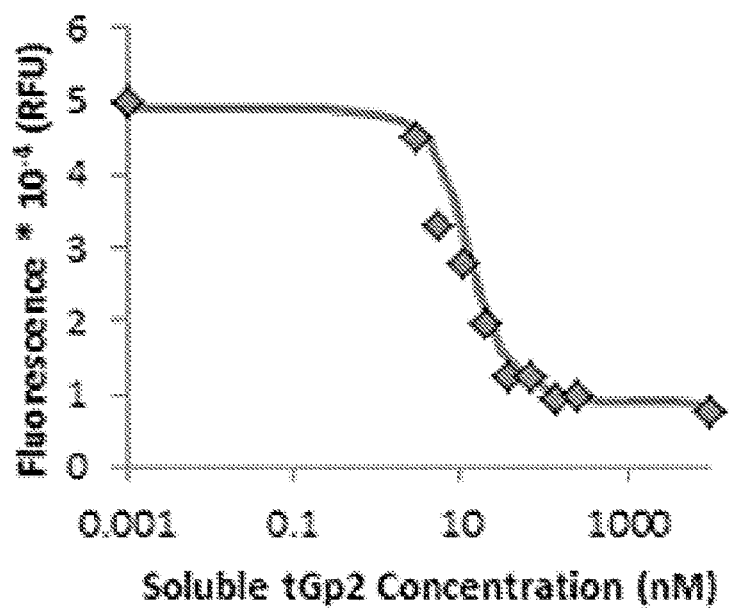
Figure 10C:
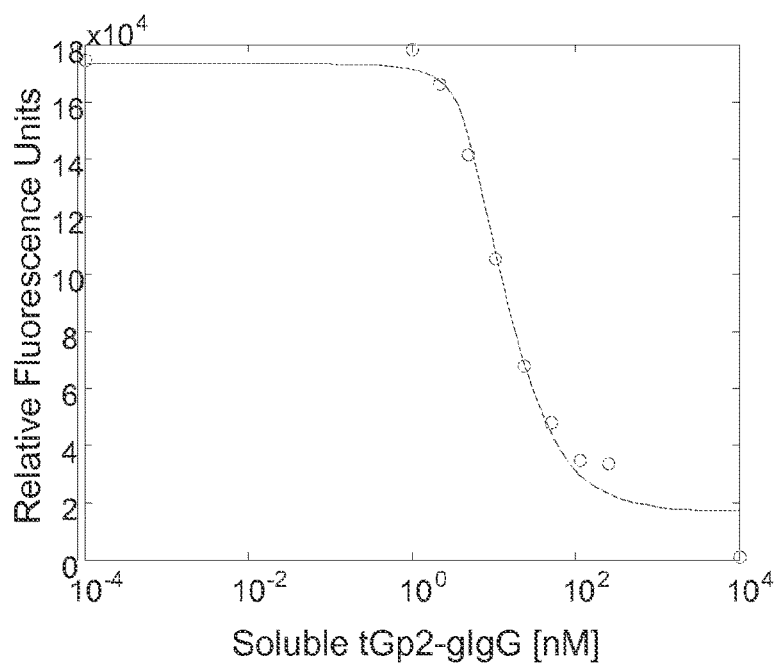

Equilibrium competition titration was used to determine the target affinity of select soluble tGp2 clones. Fluorescence was used to determine the fraction of yeast-displayed tGp2 that was bound by target that had been equilibrated with soluble tGp2 over a range of concentrations (FIG. 10). The affinities (KD) measured in this way were 0.4 nM for GaG 2.2.1 and 1.0 nM for GaR 3.2.3, showing good agreement with the $K_D$ obtained from yeast surface display affinity titration.

The Gp2 scaffold platform is flexible enough to be used to generate scaffolds that specifically bind to a variety of targets. For example, Table 1 provides amino acid sequences of variable loop regions of exemplary evolved Gp2 scaffolds that specifically bind to EGFR, goat IgG, rabbit IgG, lysozyme, and MET.

TABLE 1

| Loop 1 | SEQ ID NO: | Loop 2 | SEQ ID NO: | Scaffold Frame Mutations |
|---|---|---|---|---|
| EGFR Binders | | | | |
| SRGDSYW | 2 | PMYHIYY | 3 | W45R (GaE 2.3.3) |
| SRGDSYW | 2 | PMYHIYY | 3 | none |
| YSYAGNFA | 4 | PRSNYWCL | 5 | none |
| YCSSDP | 6 | GSDCFPLY | 7 | V31I |
| YSFYDNCL | 8 | SPYYS | 9 | E34G |
| SRGDSYW | 2 | PMYHVYY | 10 | none |
| SRGDSYW | 2 | PMYHVYY | 10 | W45R |
| YDFVSNCI | 11 | PRSNYWCL | 5 | none |
| SRGDSHW | 12 | PMYHIYY | 3 | W45R |
| SRGDSHW | 12 | PMYHIYY | 3 | none |
| YSYAGNFA | 4 | PMYHIYY | 3 | none |
| YCSSDP | 6 | GSDCFPLY | 7 | none |
| YSYAGNFA | 4 | PMYHIYY | 3 | W45R |
| SRGGSYW | 13 | PMYHIYY | 3 | none |
| SRGDSYW | 2 | PRSNYWCL | 5 | none |
| SRGDSYW | 2 | PMYHIYY | 3 | E34G, W45R |
| SRGDSYW | 2 | PMYHIYY | 3 | W45R, R56H |
| SRGDSYW | 2 | PMYHIYY | 14 | W45R |
| SRGGSYW | 13 | PMYHIYY | 3 | W45R, T55A |
| SRGDSYW | 2 | PMYYIYY | 15 | W45R |
| SRGDSYW | 2 | PMYHIYY | 3 | E44G, W45R |
| SRGDSYW | 2 | PMYHIYY | 3 | W45L |
| SRGDSYW | 2 | PMYHIYY | 3 | E41K |
| SRGDSYW | 2 | PMYHIYY | 3 | W45Q |
| SRGDSYW | 2 | PMYHIYY | 3 | E41G |
| YCSSDP | 6 | GSDCFPLY | 7 | none |
| SRGDSYW | 2 | PMYHIYY | 3 | E44K |
| Goat IgG binders | | | | |
| YDYDADYY | 16 | YSNRSDYL | 17 | E44V, Q46R (GaG 2.2.1) |
| HCYYANYT | 18 | HYPNCAIY | 19 | none |
| YDYDADYY | 16 | YSNRSDYL | 20 | none |
| RRDNDYRY | 21 | PDWTSVY | 22 | none |
| HCYYADYT | 23 | HYPNCAIY | 19 | none |
| HCHYANYT | 24 | HYPNCAIY | 19 | none |
| YDYDADYY | 16 | HYPNCAIY | 19 | none |
| HCYYANYT | 18 | HYPNCAVY | 25 | none |
| HCYYANYT | 18 | HYPNCAIH | 26 | none |
| HCYYANYT | 18 | HYPNCAIY | 19 | W45R |
| HCYYANYT | 18 | YSNRSDYL | 20 | none |
| HCYYANYT | 18 | HYPNCAIY | 19 | A18V |
| HCDYANYT | 27 | HYPNCAIY | 19 | none |
| HCYYANYT | 18 | HYPNCVIY | 28 | none |
| HCYYANYT | 18 | HYPNCAIY | 19 | V31I |
| HCYYANYA | 29 | HYPNCAIY | 19 | none |
| HCYYANYT | 18 | HYPNCAIY | 30 | none |
| HCYYANYT | 31 | HYPNCAIY | 19 | none |
| HCHYADYT | 32 | HYPNCAIY | 19 | none |
| HCYYANYT | 33 | HYPNCAIY | 19 | none |
| YCYYANYT | 34 | HYPNCAIY | 19 | none |
| HCYYADYT | 23 | HYPNCAIH | 26 | none |
| RCYYANYT | 35 | HYPNCAIY | 19 | none |
| HCYYANYT | 18 | HYPNCAIY | 19 | F27L |
| YDYDADCY | 36 | YSNRSDYL | 20 | none |
| HCYYANYT | 18 | HYPNCAIY | 19 | none |
| YDYDADYY | 16 | YSNRSDYL | 20 | A18V |
| YDYDADYY | 16 | YSNRSDYL | 20 | E44V |
| HCYYADYT | 23 | HYPNCAVY | 25 | none |
| CPYHHYC | 37 | HYPNCAIY | 19 | none |
| HCYYANYT | 18 | HYPNCAIY | 19 | E28G |
| YDYDADYY | 16 | YSDRSDYL | 38 | none |
| HCYYANYT | 18 | HYPNCAIY | 19 | T55A |
| HCYYANYT | 18 | HYPNCAIY | 19 | V29A |

TABLE 1-continued

| Loop 1 | SEQ ID NO: | Loop 2 | SEQ ID NO: | Scaffold Frame Mutations |
|---|---|---|---|---|
| HCYYANYS | 39 | HYPNCAIY | 19 | none |
| HCYYANYT | 18 | HYPNCAIY | 19 | A43V |
| HCYYANYT | 18 | PDWTSVY | 22 | none |
| HCHYANYT | 24 | HYPNCAVY | 25 | none |
| HCYYANYT | 18 | HYPNCAIY | 19 | none |
| HCYYANYT | 18 | HYPNCAIY | 19 | A33V |
| HCYYANYT | 18 | HYPNCAIY | 19 | R56H |
| HCHYANYT | 24 | HYPNCAIH | 26 | none |
| YDYDADYY | 16 | YSNRSDYL | 20 | V20I |
| HCYYANYT | 18 | HYPNCAIS | 40 | none |
| HCNYANYT | 41 | HYPNCAIY | 19 | none |
| YDYDADYY | 16 | YSSRSDYL | 42 | none |
| HCYYANYT | 18 | RYPNCAIY | 43 | none |
| HCYYANYT | 18 | HYPNCAIY | 19 | Y32H |
| YDYDADYY | 16 | YSNRSDYL | 20 | V31I |
| Rabbit IgG binders | | | | |
| HSVHGY | 44 | GNALGY | 45 | E44F, W45G (GaR 3.2.3) |
| HNVYGY | 46 | GNALGY | 45 | L42M |
| RCDHYPYS | 47 | RSNLLY | 48 | none |
| RSENGA | 49 | RSDLLY | 50 | none |
| HWNGND | 51 | RSNLLY | 48 | T19A |
| YHRNHSIP | 52 | YNDSYY | 53 | none |
| HRGDAV | 54 | RSNLLY | 48 | none |
| RCDRYPYS | 55 | RSNLLY | 48 | none |
| NYSCHLHY | 56 | PYNTHF | 57 | none |
| PNAFCKYC | 58 | EAACYGW | 59 | none |
| HDVYGY | 60 | GNALGY | 45 | W45R |
| HNAYGY | 61 | GNALGY | 45 | L42M, W45R, Q46R |
| HNVYGY | 46 | GNALGY | 45 | none |
| HNVHGY | 62 | GNALGY | 45 | L42M |
| HSVYGY | 63 | GNALGY | 45 | L42M |
| HNVYGY | 46 | GNALGY | 45 | L42M, W45R |
| YDFDHYGY | 64 | GNALGY | 45 | none |
| HNVYGY | 46 | GNALGY | 45 | V31I, L42M |
| RPGYGY | 65 | GNALGY | 45 | none |
| HNVYGY | 46 | GNALGY | 45 | T19I, L42M |
| HSVYGY | 63 | GNALGY | 45 | none |
| HNVYGY | 46 | GDALGY | 66 | L42M |
| HNVHGY | 62 | GNALGY | 45 | L42M, Q46R |
| HNAYGY | 61 | GNALGY | 45 | L42M |
| RGPYGY | 67 | GSALGY | 68 | none |
| YDGNGNGY | 69 | GNALGY | 45 | none |
| HNVYGY | 46 | GNALGY | 45 | L42M, Q46H |
| HNVYGY | 46 | GDALGY | 66 | none |
| HSVYGY | 63 | GNALGY | 45 | L42M |
| RDDDYGF | 70 | GNALGY | 45 | none |
| HGPYGY | 71 | GNALGY | 45 | none |
| HNVYGY | 46 | RSNLLY | 48 | none |
| HSVYGY | 63 | GDALGY | 66 | none |
| HRGDAV | 54 | RANLLY | 72 | none |
| HNVYGY | 46 | GSALGY | 68 | none |
| YDYDADYY | 16 | PDWTSVY | 22 | T55A |
| HDVYGY | 60 | GNALGY | 45 | L42M |
| HNVYGY | 46 | GNALGY | 45 | T19A, L42M |
| HNVYGY | 46 | GNALGY | 45 | W45R |
| HWNGND | 51 | RSNLLY | 48 | T19I, E28K |
| HRGDTV | 73 | RSDLLY | 50 | none |
| HNVYGY | 46 | GNALGY | 45 | L42M, W45R, Q46R |
| HNVHGY | 62 | GNALGY | 45 | none |
| YDYDAGYY | 74 | GNALGY | 45 | none |
| HDVHGY | 75 | GNALGY | 45 | none |
| RCDHYPYS | 47 | RSDLLY | 50 | none |
| HNVYGY | 46 | GNALGY | 45 | L42M, E44K |
| KDLHHNY | 76 | RSNLLY | 48 | none |
| HNAYGY | 61 | GKALGY | 77 | L42M |
| RCDHYPYS | 47 | GNALGY | 45 | L42M |
| YNQHFGY | 78 | GSALGY | 68 | none |
| RSENGA | 49 | GNALGY | 45 | L42M |
| CPYHHYC | 37 | GNALGY | 45 | L42M |
| HNVYGY | 46 | RSDLLY | 50 | none |
| MET binders | | | | |
| WDASDSF | 79 | SYCYP | 80 | |
| PHYRHL | 81 | YHYHPF | 82 | |
| CGLRTPTC | 83 | SYCYPYC | 84 | |

TABLE 1-continued

| Loop 1 | SEQ ID NO: | Loop 2 | SEQ ID NO: | Scaffold Frame Mutations |
|---|---|---|---|---|
| KHGDNS | 85 | SYCYPYC | 84 | |
| EYGGKC | 86 | SYCYPYC | 84 | |
| KDPYSRLM | 87 | SYCYPYC | 84 | |
| EYDGEI | 88 | SYCYPYC | 84 | |
| EDDGMI | 89 | SYCYPYC | 84 | |
| CDHSDC | 90 | SYCYPYC | 84 | |
| CDHSDC | 91 | SYCYPYC | 84 | |
| QDHDLK | 92 | SYCYPYC | 84 | V31I |
| YYHGNY | 93 | SYCYPYC | 84 | |
| YNYRFPKY | 94 | AHSGYYR | 95 | |
| YSNHHY | 96 | AGKNS Y | 97 | |
| KHGGNS | 98 | SYCYPYC | 84 | |
| Lysosyme binders | | | | |
| FSYGNL | 99 | SGAYEY | 100 | none (GaLA 0.3.2) |
| FSYGKL | 101 | SGKYEY | 102 | none |
| FSYGNL | 99 | SGKYEY | 102 | none |
| SSYGSL | 103 | SGEYEH | 104 | none |
| SSYGSL | 103 | SGEYEH | 104 | none |
| KYYDRI | 105 | SGEYEH | 104 | A18V |
| FDWVNGFY | 106 | TTDNYYD | 107 | none |
| CDAYRYC | 108 | DSNYSI | 109 | none |
| TCYTDYD | 110 | FYTICD | 111 | none |
| CNYWDC | 112 | CSNWRC | 113 | none |
| CDIYFFGC | 114 | CDDFFT | 115 | none |
| SSYSGL | 116 | SGGYEY | 117 | none |
| SSYSGL | 116 | SGEYEH | 104 | V31I |
| SSYSGL | 116 | SGEYEHV | 118 | none |
| SSYGNL | 119 | SGEYEH | 104 | none |
| FSYGSL | 120 | SGEYEH | 104 | none |
| SSYGSL | 103 | SGEYEHV | 118 | none |
| SSYGSL | 103 | SGEYEH | 104 | R56H |
| SSYGSL | 103 | SGEYEH | 104 | Q47L |
| SSYGSL | 103 | SGEYEH | 104 | E41K |
| SSYGSL | 103 | SGEYEH | 104 | E44K |
| SSYGSL | 103 | SGEYEH | 104 | T19I |
| SSYGSL | 103 | SGEYEH | 104 | V20I |
| SSYGRL | 121 | SGEYEH | 104 | none |
| CDAYRYC | 108 | DSNYSI | 109 | none |
| CPYHHYC | 37 | SGEYEH | 104 | none |
| SSYGSL | 103 | SGEYEH | 104 | E34K |
| SSYGSL | 103 | SGEYEH | 104 | E34G |
| YSYGSL | 122 | SGEYEH | 104 | none |
| SSYGSL | 103 | SGKYEH | 123 | none |
| SSYGSL | 103 | SGEYEH | 104 | P30L |
| CNYWDC | 112 | CSNWRC | 113 | none |
| CDIYFGC | 124 | CDDFFT | 115 | none |
| CSYGSL | 125 | SGEYEH | 104 | none |
| SSYGSL | 103 | SGEYEH | 104 | V29I |
| SSYGSL | 103 | SGEYEH | 104 | A43V |
| SSYGSL | 103 | SGEYEH | 104 | A33V |
| SSYGSL | 103 | SFCYPC | 126 | none |
| TCYTDYD | 110 | FYTICD | 111 | none |
| SSYGSL | 103 | SGEYEH | 104 | Y32C |
| RHLSGGY | 127 | SGEYEH | 104 | none |

Table 1 reflects particular embodiments evolved to specifically binds the indicated targets. With this information, one can combine a Loop 1 amino acid sequence with a Loop2 sequence that binds the same target to recombinantly construct an embodiment that is not reflected in the exemplified embodiments listed in Table 1. Moreover, certain loop sequences naturally appear with high frequency. These sequences may provide dominant binding character so that the amino acid sequence of the other loop in the protein scaffold is less important. For example, the Loop 2 sequence SYCYPYC (SEQ ID NO:84) occurs commonly in protein scaffolds evolved to specifically bind MET, Loop 1 sequence SRGDSYM (SEQ ID NO: 2) occurs frequently in scaffolds evolved to specifically bind EGFR, and Loop 2 sequence PMYHIYY (SEQ ID NO:3) occurs frequently in scaffolds evolved to specifically bind EGFR, demonstrating that these loop amino acid sequence can be paired with a variety of loop 1 sequences and confer MET-specific binding (in the case of SYCYPYC; SEQ ID NO:84) or EGFR-specific binding (in the case of SRGDSYM (SEQ ID NO:2) or PMYHIYY (SEQ ID NO:3). Similarly, the Loop 2 amino acid sequences GNALGY/GDALGY (SEQ ID NO:45)/ (SEQ ID NO:66) occur frequently in protein scaffolds evolved to specifically bind rabbit IgG, indicating that these loop amino acid sequences and conservatively substituted variations thereof—can be paired with a variety of loop 1 sequences and confer rabbit IgG-specific binding. A similar analysis can be performed of loop sequences evolved to specifically bind any particular target of interest to determine which loop sequences may be more versatilely paired with a broader range of loop sequences and specifically bind the desired target.

Figure 11:
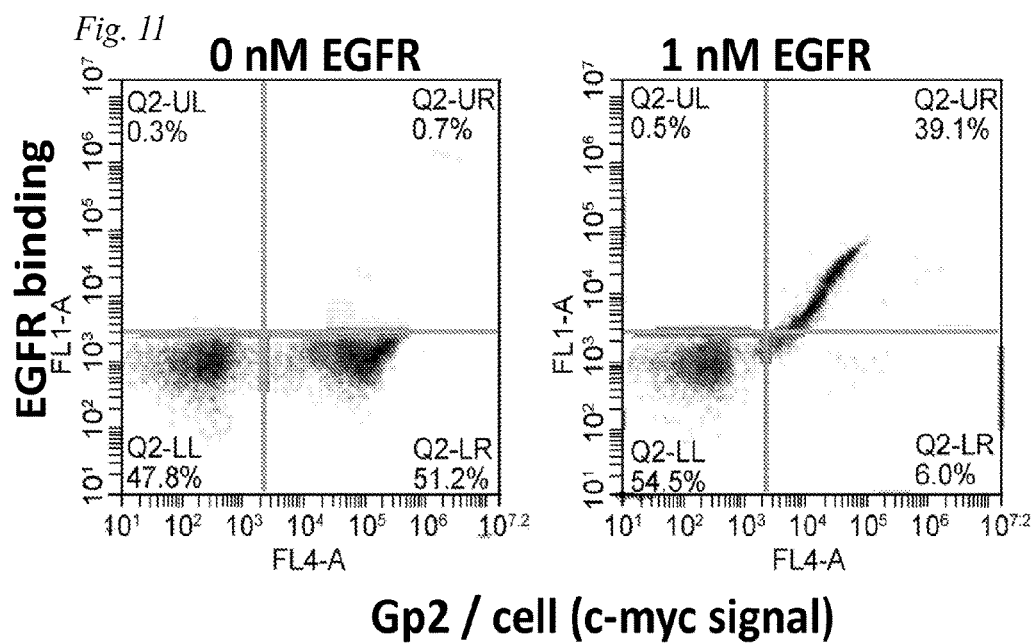
FIG. 11. Yeast displaying Gp2 anti-EGFR (GaE 2.3.3) effectively bind 1 nM soluble EGFR ectodomain.
Figure 12:
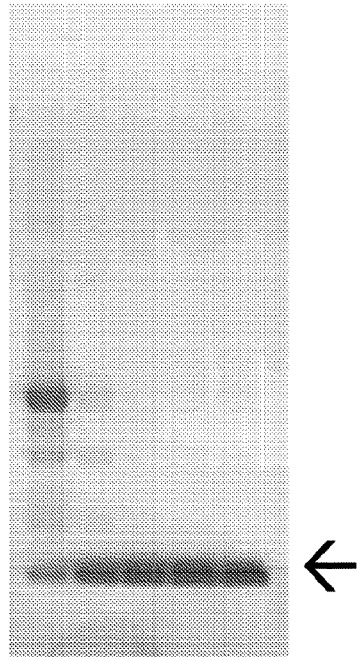
FIG. 12. Evolved Gp2 domain is readily produced recombinantly in *E. coli* shake flask culture. (A) Purified Gp2 indicated at arrow; (B) Gp2 purified by metal affinity chromatography as assessed by mass spectrometry.
Figure 12:
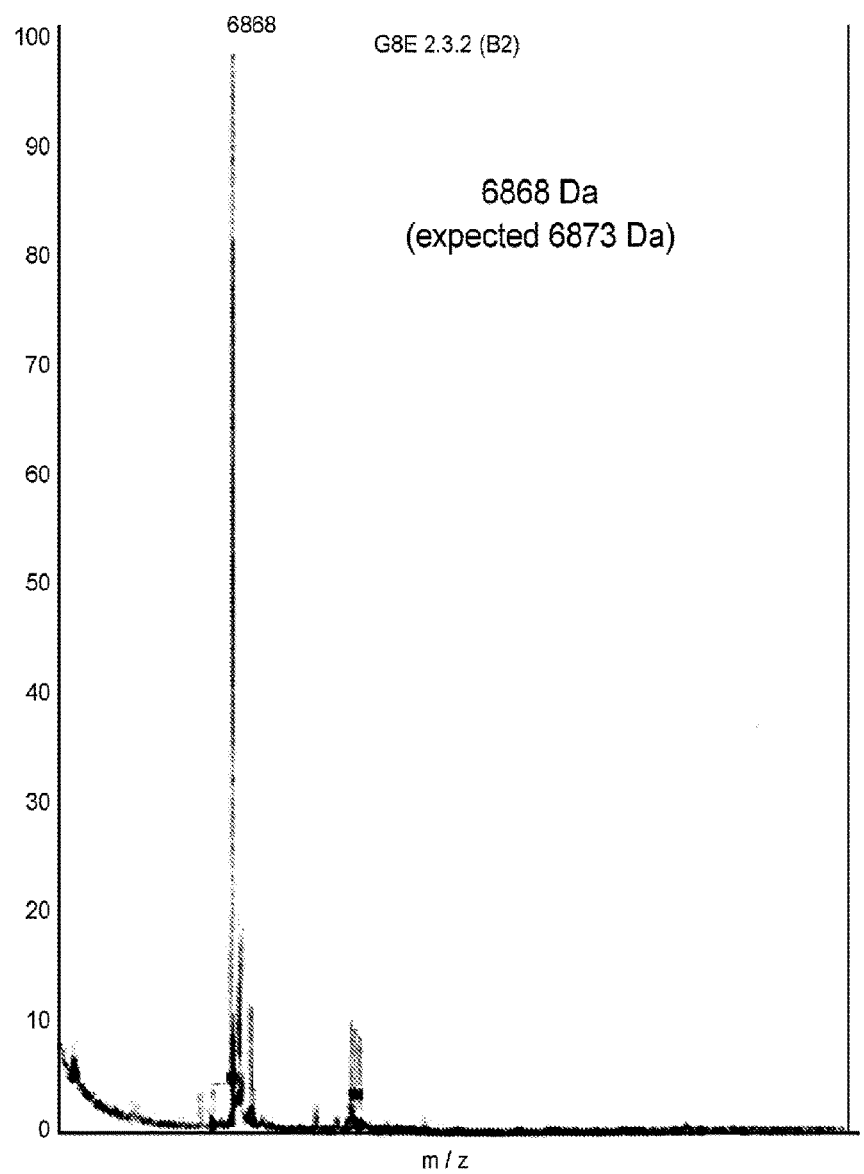
Figure 13:
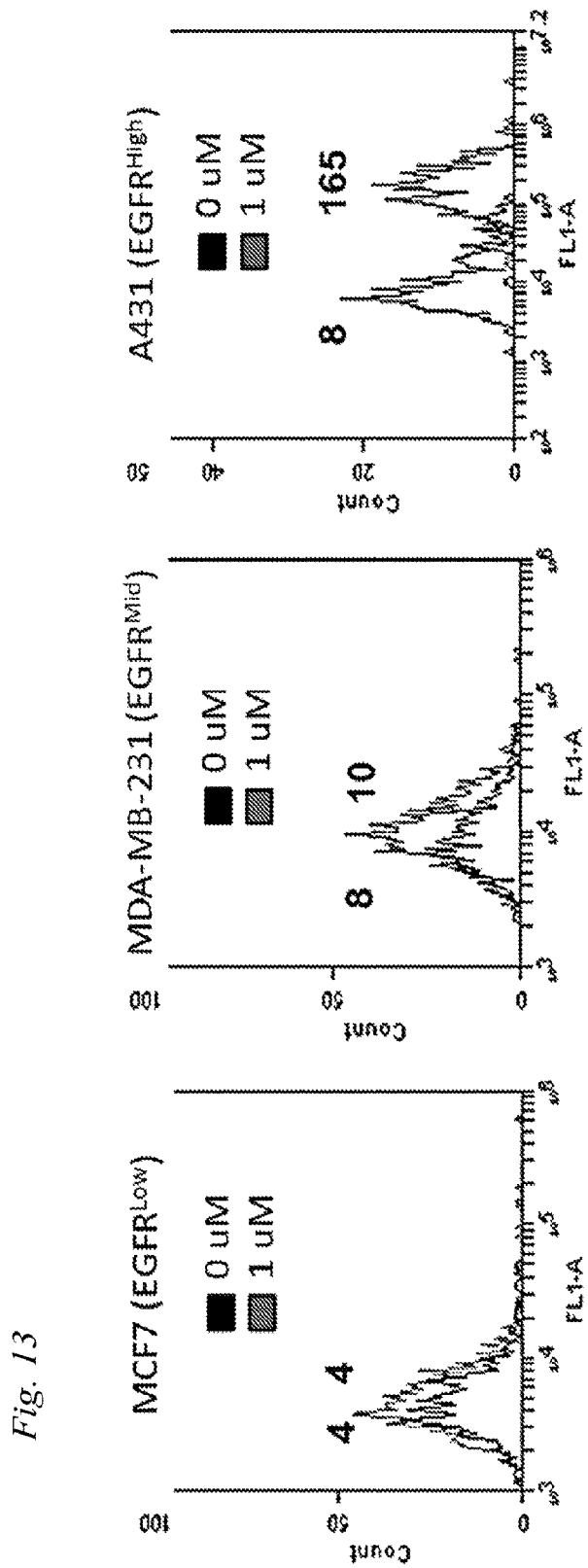
FIG. 13. Evolved Gp2 domain binds to human cancer cell lines in an EGFR-dependent manner. The indicated cell types were incubated with 0 or 1 µM Gp2 anti-EGFR. Binding was detected by flow cytometry.
Figure 14:
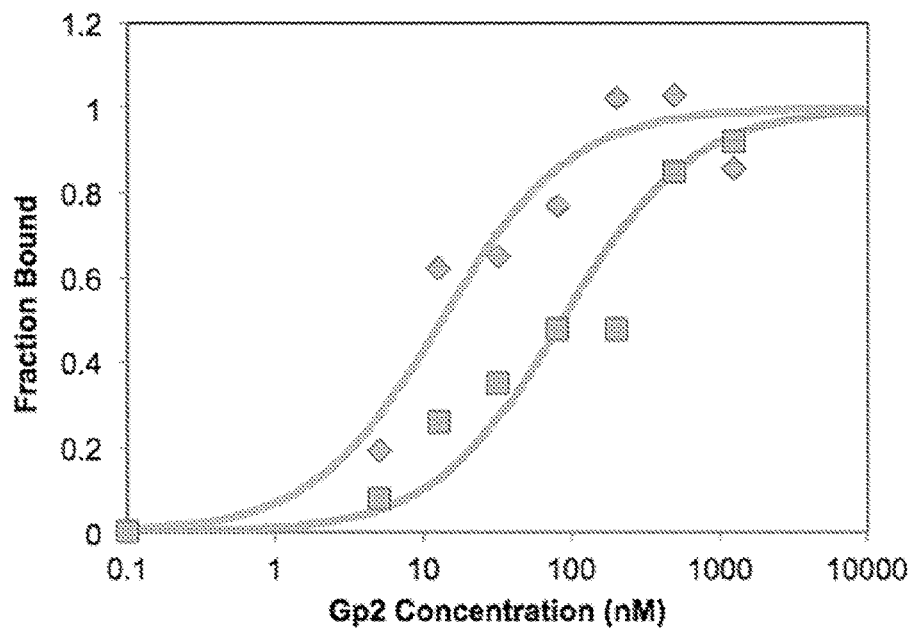
FIG. 14. Evolved Gp2 domain binds to human cancer cell line. A431 cells were incubated with the indicated concentration of Gp2 anti-EGFR (with His tag). Binding was detected with anti-His6-FITC and flow cytometry. One experiment yielded a 13 nM affinity. Another experiment yielded 87 nM. The average is 50 nM.
Figure 15:
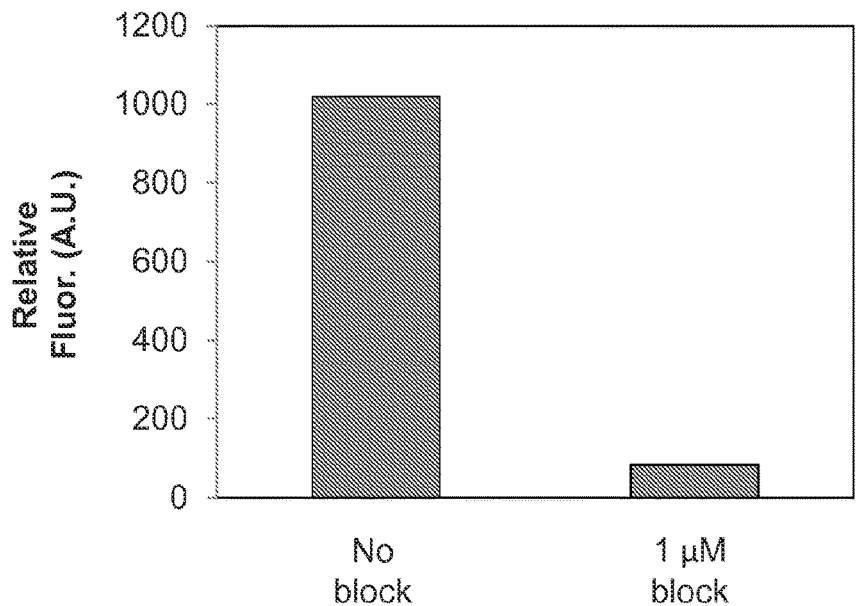
FIG. 15. Evolved Gp2 domain binding can be blocked by non-labeled evolved Gp2 domain. The addition of 1 µM of unlabeled Gp2 blocks binding of labeled Gp2 to A431 cells.
Figure 16:
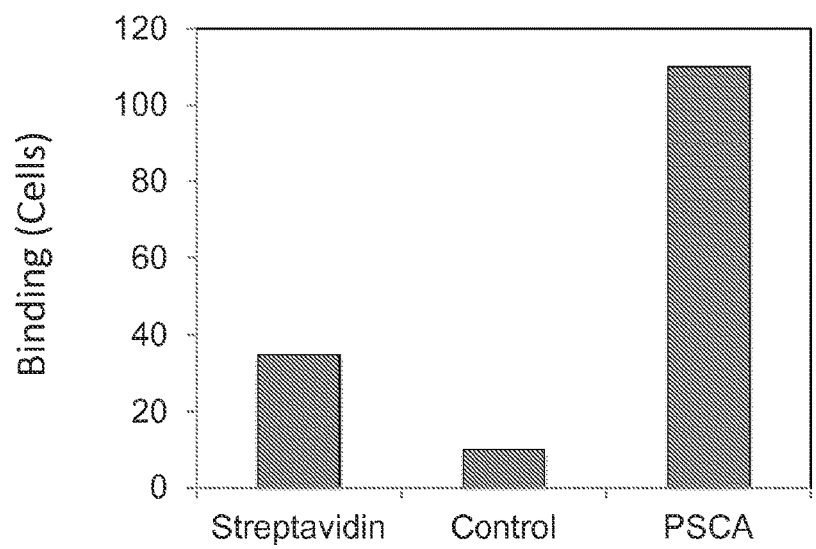
FIG. 16. Evolved Gp2 domains bind preferentially to prostate stem cell antigen (PSCA).
Figure 17A:
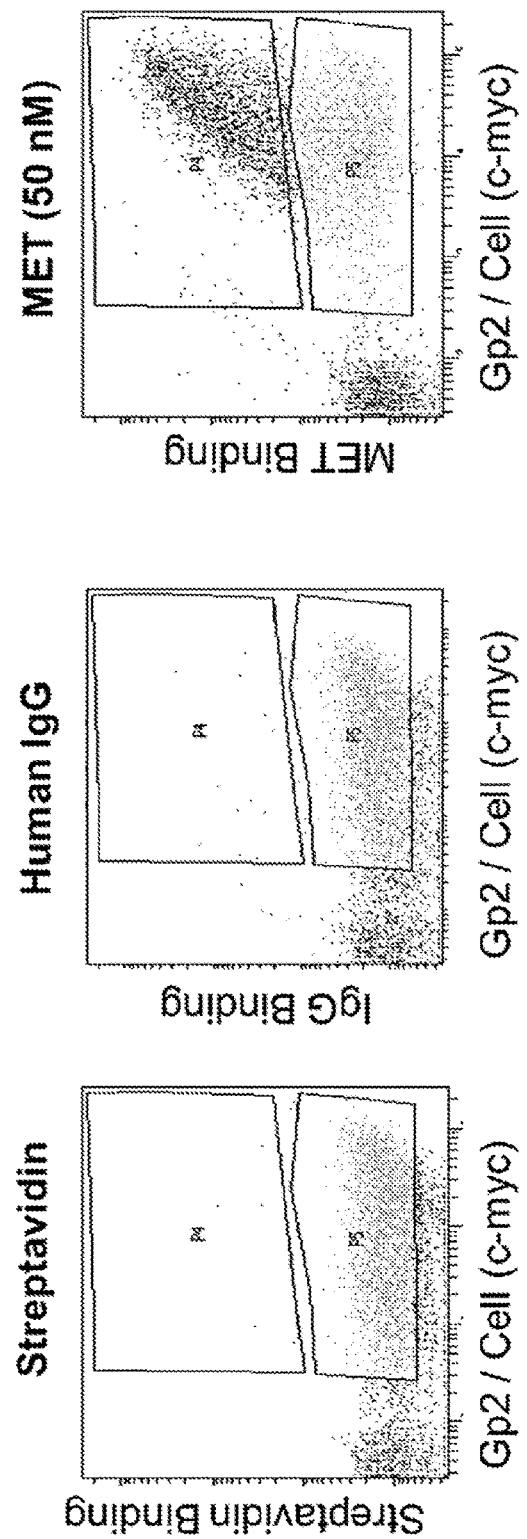
FIG. 17. (A) Evolved Gp2 domains bind specifically to soluble mesenchymal epithelial transition (MET or c-Met), also known as hepatocyte growth factor receptor; (B) Sequences of Gp2 domains that bind MET (SEQ ID NOs: 136-140 from top to bottom) and a consensus sequence (SEQ ID NO:135).
Figure 17B:
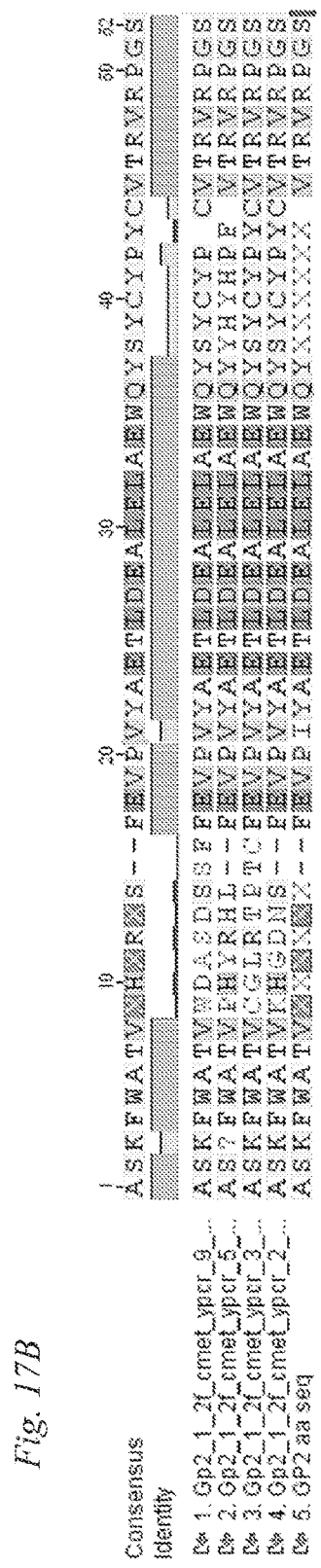
Figure 18A:
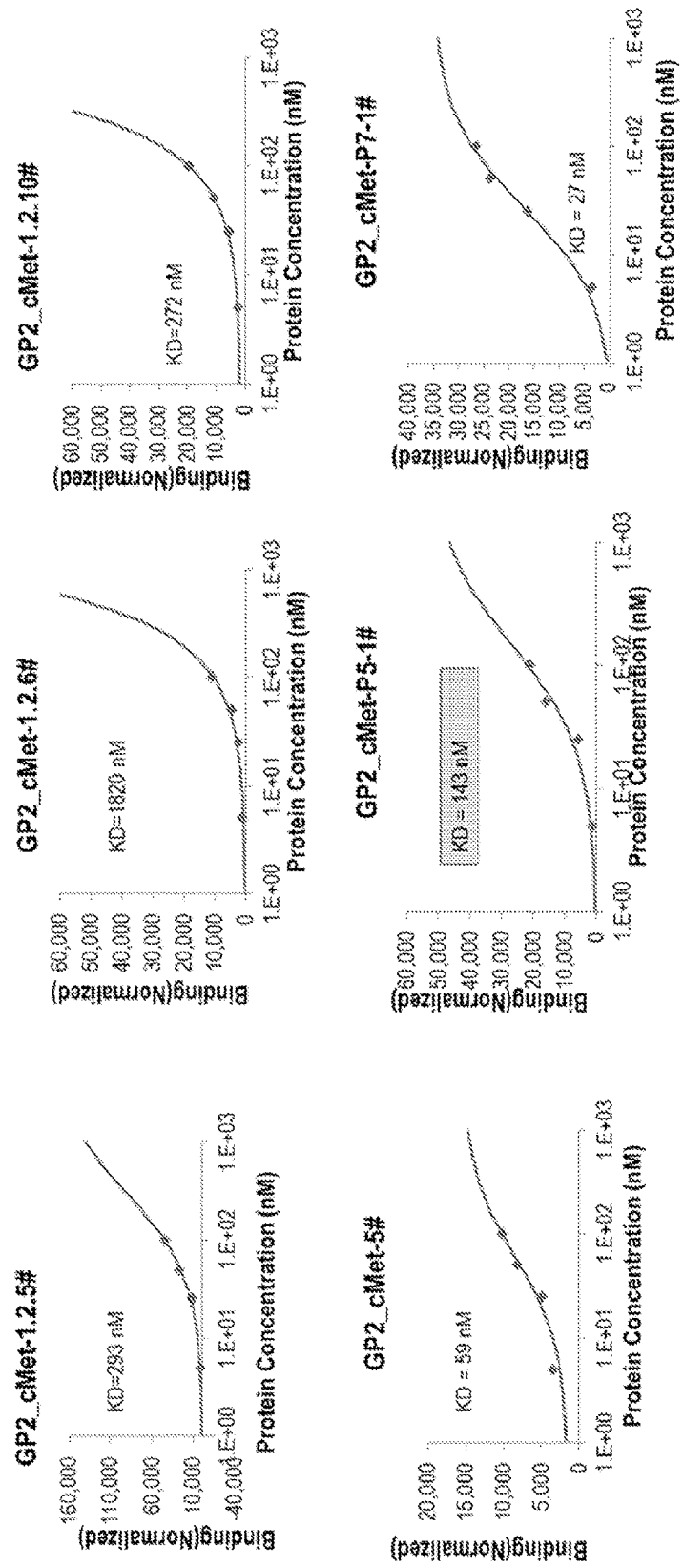
FIG. 18. (A) Affinity titrations indicate a 27 nM K$_d$ for MET-binding protein scaffold; (B). Purified Gp2 binds A431 cells, which express MET. (C) Purified Gp2 does not exhibit non-specific binding to MET-CHO cells.
Figure 18B:
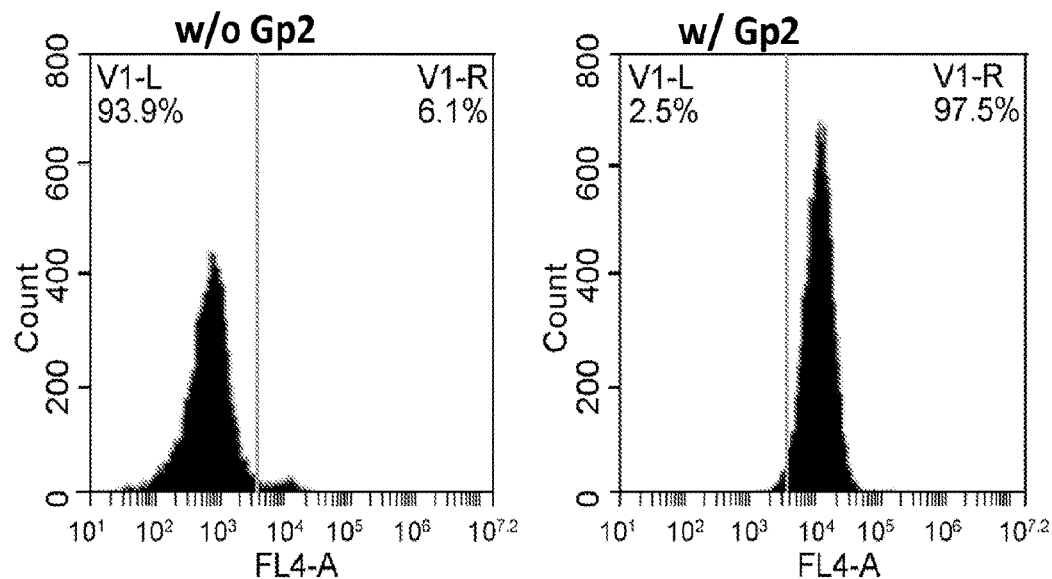
Figure 18C:
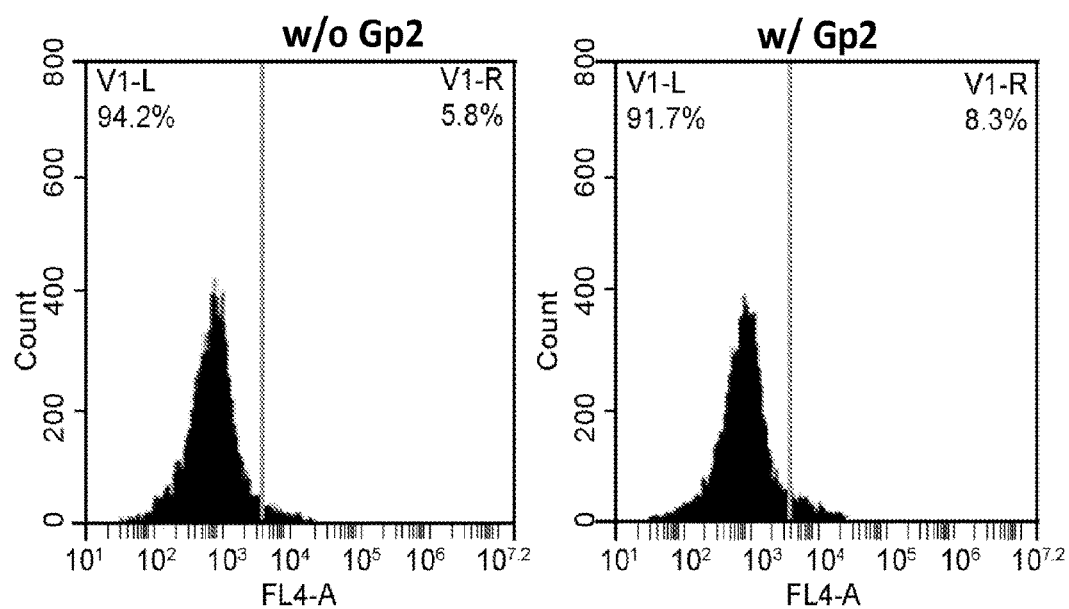

FIG. 11 and FIG. 13 show specific binding character of an exemplary EGFR-specific tGp2 protein scaffold (GaE 2.3.3, Table 1). FIG. 16 shows binding of an evolved Gp2 scaffold that specifically binds prostate stem cell antigen (PSCA). FIG. 17B illustrates amino acid sequences of evolved Gp2 scaffolds that specifically bind mesenchymal epithelial transition (MET)/hepatocyte growth factor receptor (HGFR)/scatter factor receptor (SFR) (MET/HGFR/SFR) (FIG. 17A). Evolved MET binders exhibit 27 nM affinity by titration (FIG. 18A) and are specific for binding MET-expressing cells (FIG. 18B and FIG. 18C).

Figure 19A:
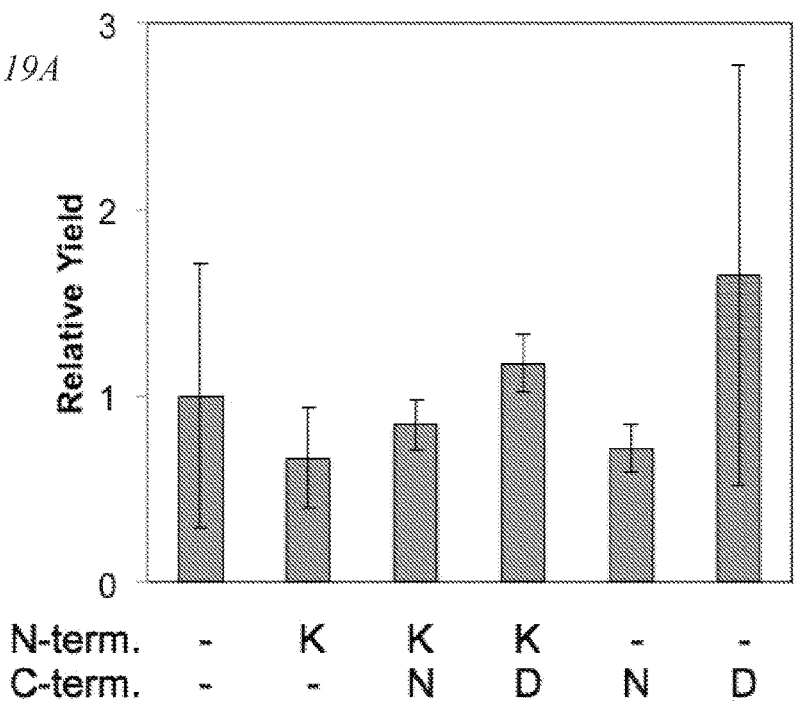
FIG. 19. Wild-type Gp2 was produced in *E. coli* with the indicated modifications to the N- and C-termini. (A) Relative production yields from the soluble fraction of *E. coli* are indicated. (B) Concentration of Gp2 in solution after centrifugation of saturated solution.
Figure 19B:
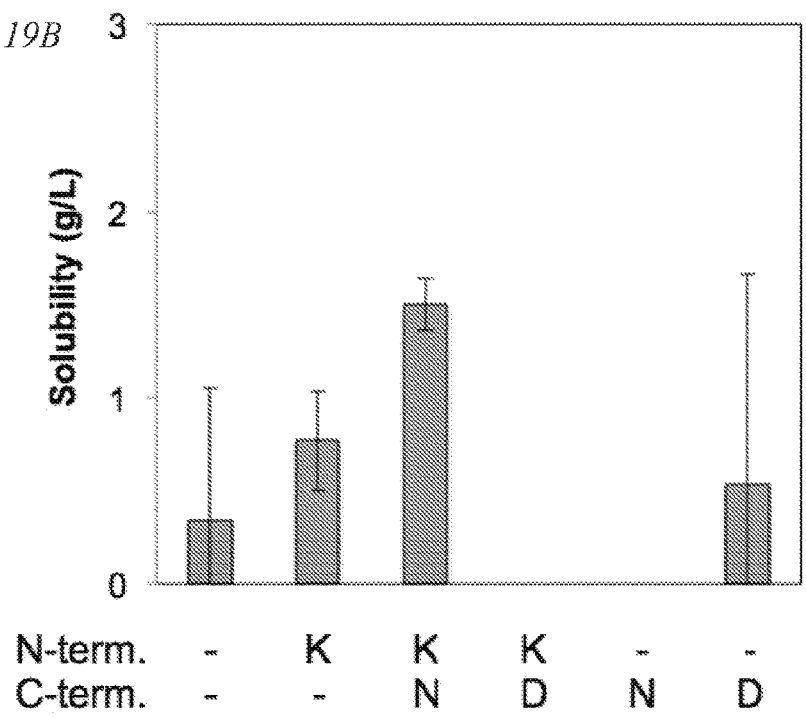
Figure 20:
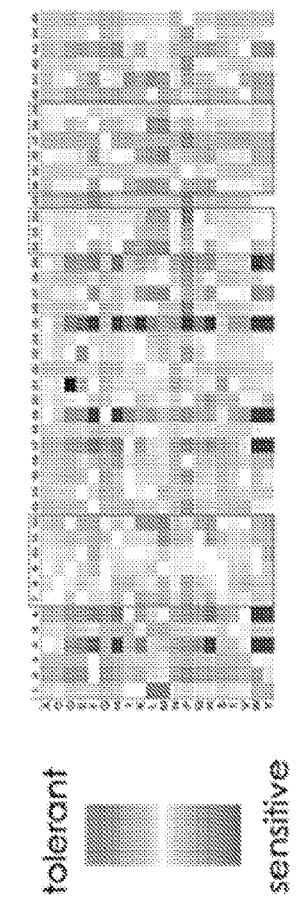
FIG. 20. The (de)stabilization upon mutation of Gp2 library members was analyzed by FoldX for all single site mutations. A Gp2 library clone was randomly selected in silico, and used as the basis to calculate the change in stability upon single site mutation. At least 50 library clones were considered for every site/amino acid combination. The median stability is presented in the heat map and on the structures. This information can be used to predict stabilizing mutants.
Figure 20:
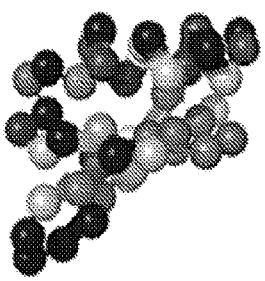
Figure 20:
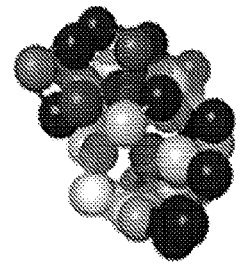

The N-terminus and/or the C-terminus of the scaffold may be modified to generate alternative sequences that may present unique properties including, for example, improved yield from recombinant production, improved solubility, and/or modified physiological distribution. For example, addition of lysine to the N-terminus and/or addition of asparagine or aspartic acid to the C-terminus of Gp2 can modulate the recombinant yield and solubility of the protein (FIG. 19). Indeed, FIG. 20 provides data suggesting scaffold frame mutations and loop library design strategies that will yield a more stable protein.

Thus, while described above in the context of exemplary embodiments in which the scaffolds possess structural domains that typically reflect the native, though truncated, Gp2 amino acid sequence, a scaffold may be prepared in which the Gp2 structural domain may be derived from Gp2—i.e., exhibit one or more amino acid additions, amino acid substitutions, amino acid deletions, and/or post-translational modifications compared to a native Gp2 amino acid sequence.

Thus, while described above in the context of exemplary embodiments in which the scaffolds specifically bind to exemplary targets, a scaffold may be prepared to specifically bind to—and the methods of using the scaffold so made may involve binding to—any suitable target. Exemplary binding targets include, for example, epidermal growth factor receptor (EGFR), mesenchymal epithelial transition (MET), prostate stem cell antigen (PSCA), death receptor, insulin-like growth factor 1 receptor (IGF1R), insulin receptor, tumor necrosis factor (TNF), tumor necrosis factor receptor (TNFR), vascular endothelial growth factor (VEGF), vascular endothelial growth factor receptor 2 (VEGFR2), carcinoembryonic antigen (CEA), thymocyte antigen 1 (Thy1; CD90), CD276, programmed cell death receptor (PD-1), fibroblast growth factor (FGF), human epidermal growth factor receptor 2 (HER2), prostate-specific membrane antigen (PSMA), a claudin family (e.g., claudin 3, claudin 4, and claudin 7), a mucin (e.g., mucin-1 and mucin-4), endosialin (Tem1), endoglin (CD105), urokinase receptor, an annexin, CD55, carcinoembryonic antigen-related cell adhesion molecule 6 (CEACAM6), CD44, CD47, CXCR4, CD24, receptor tyrosine-protein kinase erbB-3 (HER3), epithelial cell adhesion molecule (EpCAM), estrogen receptor (ER), progesterone receptor (PR, NR3C3), and neurological and/or cardiovascular biomarkers.

In another aspect, this disclosure describes protein display libraries that include a plurality of protein scaffolds as described above. The libraries may be useful for capturing and identifying target binding scaffolds and therefore facilitate building multimeric scaffolds.

A multimeric scaffold can include at least two scaffolds as described above. In some embodiments, the multimeric scaffolds can include at least two scaffolds linked by, for example, a dimerization domain, an amino acid linker, a disulfide bond, a chemical crosslink, and IgG molecule or fragment thereof, or an Fc region. The term "multimeric" refers to at least two or more scaffolds in association and can include, for example, at least two scaffolds, at least three scaffolds, at least four scaffolds, or more scaffolds.

In some embodiments, a multimeric scaffold can include scaffolds that are specific for the same epitope. In other embodiments, a multimeric scaffold can include scaffolds that are specific for different epitopes. A multimeric scaffold may be linked by any suitable linker A suitable linker for a specific case where two or more scaffolds are to be connected may depend, at least in part, on parameters such as, for example, the nature of the scaffold proteins, and/or the stability of the peptide linker towards proteolysis and oxidation.

A linker polypeptide may predominantly include the amino acid residues Gly, Ser, Ala, and/or Thr. For example, at least 75% of the amino acids in a peptide linker such as, for example, at least 80%, at least 85%, or at least 90% of amino acid residues in a peptide linker may be Gly, Ser, Ala and/or Thr. In some embodiments, a peptide linker may also consist only of of Gly, Ser, Ala and/or Thr residues. A linker polypeptide can have a length adequate to link two or more scaffold proteins or two or more multimeric scaffolds in such a way that they assume the correct conformation relative to one another so that they retain the desired activity.

In another aspect, this disclosure describes a method of identifying the amino acid sequence of a protein scaffold capable of binding to target so as to form a scaffold:target complex. In one embodiment, the method can include providing a protein scaffold display library as described herein, contacting this original protein scaffold display library with an immobilized or separable target, separating the scaffold: target complexes from the free scaffolds, and causing the replication of the separated scaffolds to produce a new protein scaffold display library distinguished from the original protein scaffold library by having a lowered diversity and by being enriched in displayed scaffolds capable of binding the target. In some embodiments, the method can include repeating the method using the "new" protein scaffold library as the "original" protein scaffold library in a subsequent generation of performing the method.

In some embodiments, the protein scaffolds may be further randomized after identification from a library screen. In one embodiment, the method can include, therefore, further randomizing at least one of the loop regions of a protein scaffold. The further randomized protein scaffolds may then be used as the "original" protein scaffold library in a subsequent generation of performing the method.

In other aspects, this disclosure therefore provides methods of making, using, screening, optimizing, and engineering the protein scaffolds and protein scaffold libraries.

In yet another aspect, this disclosure provides pharmaceutical compositions that include one or a combination of protein scaffolds described herein, formulated together with a pharmaceutically acceptable carrier. Such compositions may include one or a combination of, for example, two or more different protein scaffolds. For example, a pharmaceutical composition of the invention may include a combination of scaffolds that bind to different epitopes on the target antigen or that have complementary activities.

A pharmaceutical composition can be administered in combination therapy—i.e., combined with other agents. For example, a combination therapy can include a protein scaffold as described herein combined with at least one other therapy wherein the therapy may be immunotherapy, chemotherapy, radiation treatment, or drug therapy.

A pharmaceutical composition may include one or more pharmaceutically acceptable salts. Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition also, or alternatively, may include a pharmaceutically acceptable anti-oxidant. Examples of pharmaceutically acceptable antioxidants include water soluble antioxidants such as, for example, ascorbic acid, cysteine hydrochloride, sodium bisulfate, sodium metabisulfite, sodium sulfite, and the like; oil-soluble antioxidants such as, for example, ascorbyl palmitate, butylated hydroxyanisole (BHA), butylated hydroxytoluene (BHT), lecithin, propyl gallate, alpha-tocopherol, and the like; and/or metal chelating agents such as, for example, citric acid, ethylenediamine tetraacetic acid (EDTA), sorbitol, tartaric acid, phosphoric acid, and the like.

A pharmaceutical composition also, or alternatively, may include an aqueous or non-aqueous carrier. Examples of suitable aqueous and non-aqueous carriers that may be employed in a pharmaceutical compositions include, for example, water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

A pharmaceutical composition also, or alternatively, may include one or more adjuvants such as, for example, a preservative, a wetting agent, an emulsifying agent, and/or a dispersing agent. In some embodiments, a pharmaceutical composition can include an antibacterial agent and/or an antifungal agent such as, for example, paraben, chlorobutanol, phenol sorbic acid, and the like. It may also be desirable to include isotonic agents, such as sugars, sodium chloride, polyalcohols such as mannitol, sorbitol and the like into the compositions. In addition, prolonged absorption of an injectable pharmaceutical form may be provided by including an agent that delays absorption such as, for example, aluminum monostearate or gelatin.

A pharmaceutical composition typically is prepared to be sterile and stable under the conditions of manufacture and storage. A pharmaceutical composition can be formulated as a solution, microemulsion, liposome, or other ordered structure suitable to high drug concentration. A sterile injectable solution can be prepared by incorporating one or more protein scaffolds—including in some instances, one or more multimeric scaffolds—in an effective amount in an appropriate solvent with one or a combination of ingredients enumerated above, as desired, followed by sterilization microfiltration. Generally, a dispersion can be prepared by incorporating one or more protein scaffolds—including in some instances, one or more multimeric scaffolds—into a sterile vehicle that contains a basic dispersion medium and any other desired ingredients from those enumerated above. In the case of sterile powders for the preparation of sterile injectable solutions, vacuum drying and/or freeze-drying (lyophilization) can yield a powder of one or more protein scaffolds—including in some instances, one or more multimeric scaffolds—plus any additional desired ingredient from a previously sterile-filtered solution thereof.

To prepare pharmaceutical or sterile compositions including a protein scaffold, the protein scaffold can be mixed with a pharmaceutically acceptable carrier or excipient. Formulations of therapeutic and diagnostic agents can be prepared by mixing with physiologically acceptable carriers, excipients, or stabilizers in the form of, e.g., lyophilized powders, slurries, aqueous solutions, lotions, or suspensions (see, e.g., Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y.).

Determining an appropriate dose can involve, for example, using parameters or factors known or suspected in the art to affect treatment or predicted to affect treatment. Generally, one can begin with an amount somewhat less than the anticipated optimum dose and thereafter increase the dose by small increments until the desired effect is achieved relative to any negative side effects.

Actual dosage levels of the active ingredients in a pharmaceutical composition as described herein may be varied so as to obtain an amount of the active ingredient that is effective to achieve the desired therapeutic response for a particular patient, composition, and mode of administration, without being toxic to the patient. The selected dosage level may depend, at least in part, upon a variety of pharmacokinetic factors including, for example, the activity of the particular composition being administered, the route of administration, the time of administration, the rate of clearance of the particular protein scaffold being employed, the duration of the treatment, other drugs, compounds and/or materials present in the pharmaceutical composition, the age, sex, weight, condition, general health and prior medical history of the patient being treated, and like factors well known in the medical arts.

An effective dose of a small molecule therapeutic such as a protein scaffold is typically about the same as for an antibody or polypeptide on a molar basis, but lower dose may be effective on a mass basis. Moreover, still lower doses may be effective for diagnostic applications. Thus, a minimum effective dose can be at least 100 pg/kg body weight such, for example, at least 0.2 ng/kg, at least 0.5 ng/kg, at least 1.0 ng/kg, at least 10 ng/kg, at least 100 ng/kg, at least 0.2 µg/kg, at least 0.5 µg/kg, at least 1.0 µg/kg, at least 2.0 µg/kg, at least 10 µg/kg, at least 25 µg/kg, at least 100 µg/kg, at least 0.2 mg/kg, at least 0.5 mg/kg, at least 1.0 mg/kg, at least 2.0 mg/kg, at least 5.0 mg/kg, at least 10 mg/kg, at least 25 mg/kg, or at least 50 mg/kg (see, e.g., Yang, et al. 2003. New Engl. J. Med. 349:427-434; Herold, et al. 2002. New Engl. J. Med. 346:1692-1698; Liu, et al. 1999. J. Neurol. Neurosurg. Psych. 67:451-456; and Portielji, et al. 2003. Cancer Immunol. Immunother. 52:133-144). In some embodiments, the dosage may be, for example, from 0.1 µg/kg to 20 mg/kg, from 0.1 µg/kg to 10 mg/kg, from 0.1 µg/kg to 5 mg/kg, from 0.1 to 2 mg/kg, from 0.1 µg/kg to 1 mg/kg, from 0.1 µg/kg to 0.75 mg/kg, from 0.1 µg/kg to 0.5 mg/kg, from 0.1 µg/kg to 0.25 mg/kg, from 0.1 µg/kg to 0.15 mg/kg, from 0.1 µg/kg to 0.10 mg/kg, from 0.1 µg/kg to 0.5 mg/kg, from 0.01 mg/kg to 0.25 mg/kg, or from 0.01 mg/kg to 0.10 mg/kg of the patient's body weight.

Alternatively, the dose may be calculated using actual body weight obtained just prior to the beginning of a treatment course. For the dosages calculated in this way, body surface area (m$^2$) is calculated prior to the beginning of the treatment course using the Dubois method: m$^2$=(wt kg$^{0.425}$×height cm$^{0.725}$)×0.007184.

In some embodiments, the protein scaffold may be administered, for example, from a single dose to multiple doses per week, although in some embodiments the method can be performed by administering the protein scaffold at a frequency outside this range. In certain embodiments, the protein scaffold may be administered from about once per month to about five times per week.

A composition may also be administered via one or more routes of administration using one or more of a variety of methods known in the art. As will be appreciated by the skilled artisan, the route and/or mode of administration will vary depending upon the desired results. Exemplary routes of administration for scaffolds of the invention include intravenous, intramuscular, intradermal, intraperitoneal, subcutaneous, spinal or other parenteral routes of administration, for example by injection or infusion. Parenteral administration may represent modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, a composition of the invention can be administered via a non-parenteral route, such as a topical, epidermal or mucosal route of administration, for example, intranasally, orally, vaginally, rectally, sublingually or topically.

If a pharmaceutical composition that includes one or more protein scaffolds described herein is administered in a controlled release or sustained release system, a pump may be used to achieve controlled or sustained release. Alternatively, polymeric materials can be used to achieve controlled or sustained release of a pharmaceutical composition that includes a protein scaffold. Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In one embodiment, the polymer used in a sustained release formulation is inert, free of leachable impurities, stable on storage, sterile, and biodegradable. A controlled or sustained release system can be placed in proximity of the prophylactic or therapeutic target, thus requiring less of the therapeutic protein scaffold composition in order to achieve the desired therapy.

If the protein scaffold described herein is administered topically, it can be formulated in the form of an ointment, cream, transdermal patch, lotion, gel, shampoo, spray, aerosol, solution, emulsion, or other form well-known to one of skill in the art. For non-sprayable topical dosage forms, viscous to semi-solid or solid forms comprising a carrier or one or more excipients compatible with topical application and having a dynamic viscosity, in some instances, greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, in some instances, in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms if desired. Examples of such additional ingredients are well-known in the art.

If the protein scaffold described herein is administered intranasally, it can be formulated in an aerosol form, spray, mist or in the form of drops. In particular, prophylactic or therapeutic agents for use according to the present invention can be conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

Methods of Using Protein Scaffolds

In yet another aspect, this disclosure provides imaging methods and methods of treating, ameliorating, detecting, diagnosing, or monitoring a disease or a symptom or clinical sign thereof, as described herein, in a patient by administering therapeutically effective amounts of a protein scaffold described herein and/or a pharmaceutical composition that includes one or more protein scaffolds described herein.

As used herein, the term "treating" and variations thereof refer to reducing, limiting progression, ameliorating, or resolving, to any extent, the symptoms or clinical signs related to a condition. A "symptom" refers to any subjective evidence of disease or of a patient's condition; a "sign" or "clinical sign" refers to an objective physical finding relating to a particular condition capable of being found by one other than the patient. A "treatment" may be therapeutic or prophylactic. "Therapeutic" and variations thereof refer to a treatment that ameliorates one or more existing symptoms or clinical signs associated with a condition. "Prophylactic" and variations thereof refer to a treatment that limits, to any extent, the development and/or appearance of a symptom or clinical sign of a condition. Generally, a "therapeutic" treatment is initiated after a condition manifests in a subject, while "prophylactic" treatment is initiated before a condition manifests in a subject. Prophylactic treatment may be administered to a subject at risk of having a condition. "At risk" refers to a subject that may or may not actually possess the described risk. Thus, for example, a subject "at risk" of infection by a microbe is a subject present in an area where individuals have been identified as infected by the microbe and/or is likely to be exposed to the microbe even if the subject has not yet manifested any detectable indication of infection by the microbe and regardless of whether the subject may harbor a subclinical amount of the microbe. In the case of a non-infectious condition, for example, a subject "at risk" for developing a specified condition is a subject that possesses one or more indicia of increased risk of having, or developing, the specified condition compared to individuals who lack the one or more indicia, regardless of the whether the subject manifests any symptom or clinical sign of having or developing the condition.

The protein scaffolds described herein may have utility in molecular imaging applications including, for example, both traditional molecular imaging techniques (e.g., magnetic resonance imaging (MRI), positron emission tomography (PET), single photon emission computed tomography (SPECT), ultrasound, photoacoustic, and fluorescence) and microscopy and/or nanoscopy imaging techniques (e.g., total internal reflection fluorescence (TIRF)-microscopy, stimulated emission depletion (STRED)-nanoscopy, and atomic force microscopy (AFM).

The protein scaffolds described herein have in vitro and in vivo detection, diagnostic, and/or therapeutic utilities. For example, a protein scaffold may be included in a detection composition for use in a detection method. The method generally can include allowing a protein scaffold that specifically binds to a target of interest with a sample that includes the target of interest, then detecting the formation of a protein scaffold:target complex. Thus, the protein scaffold may be designed to include a detectable marker such as, for example, a radioactive isotope, a fluorescent marker, an enzyme, or a colorimetric marker. As another example, the protein scaffolds described herein can be administered to cells in culture, e.g. in vitro or ex vivo, or in a subject, e.g., in vivo, to treat—either therapeutically or prophylactically—or diagnose a variety of disorders.

This disclosure further provides the use of the scaffolds described herein for prophylaxis, diagnosis, management, treatment, or amelioration of one or more symptoms and/or clinical signs associated with diseases or disorders including, but not limited to, cancer, inflammatory and autoimmune diseases, infectious diseases, either alone or in combination with other therapies.

Moreover, many cell surface receptors activate or deactivate as a consequence of crosslinking of subunits. The protein scaffolds described herein may be used to stimulate or inhibit a response in a target cell by crosslinking of cell surface receptors. In another embodiment, a protein scaffold as described herein may be used to block the interaction of multiple cell surface receptors with antigens. In another embodiment, a protein scaffold as described herein may be used to strengthen the interaction of multiple cell surface receptors with antigens. In another embodiment, it may be possible to crosslink a homodimer and/or heterodimer of a cell surface receptor using a protein scaffold as described herein that includes binding domains that share specificity for the same antigen, or bind two different antigens. In another embodiment, a protein scaffold as described herein could be used to deliver a ligand, or ligand analogue to a specific cell surface receptor.

The disclosure further provides methods of targeting epitopes not easily accomplished with traditional antibodies. For example, in one embodiment, a protein scaffold as described herein may be used to first target an adjacent antigen and while binding, another binding domain may engage the cryptic antigen.

This disclosure also provides methods of using a protein scaffold to bring together distinct cell types. In one embodiment, a protein scaffold as described herein may bind a target cell with one binding domain and recruit another cell via another binding domain. In another embodiment, the first cell may be a cancer cell and the second cell is an immune effector cell such as an NK cell. In another embodiment, a protein scaffold as described herein may be used to strengthen the interaction between two distinct cells, such as an antigen presenting cell and a T cell to possibly boost the immune response.

This disclosure also provides methods of using scaffolds proteins to ameliorate or treat, either prophylactically or therapeutically, cancer or a symptom or clinical sign thereof. In various embodiments, the methods may be useful in the treatment of cancers of the head, neck, eye, mouth, throat, esophagus, chest, skin, bone, lung, colon, rectum, colorectal, stomach, spleen, kidney, skeletal muscle, subcutaneous tissue, metastatic melanoma, endometrial, prostate, breast, ovaries, testicles, thyroid, blood, lymph nodes, kidney, liver, pancreas, brain, or central nervous system.

This disclosure further provides methods of using protein scaffolds to deplete a cell population. In one embodiment, such a method may be used to deplete one or more of the following cell types: eosinophil, basophil, neutrophil, T cell, B cell, mast cell, monocytes and tumor cell.

As used herein, the term "and/or" means one or all of the listed elements or a combination of any two or more of the listed elements; the terms "comprises" and variations thereof do not have a limiting meaning where these terms appear in the description and claims; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Library Construction

Library design and construction was carried out as described previously (Hackel et al, *J Mol Biol,* 2010, 401: 84-96). Briefly, degenerate nucleotides were designed to provide the desired CDR-inspired amino acid distribution at each position in the scaffold loops. At diversified positions (FIG. 4) the mixtures of nucleotides were: 15% A and C, 25% G, and 45% T in the first position; 45% A, 15% C, 25% G, and 15% T in the second position; and 45% C, 10% G, and 45% T in the third position. This mixture of nucleotides resulted in a theoretical amino acid composition of 17% Y, 13% S, 11% D, 9% N, 6% A and H, 5% C and T, 4% G and P, 3% F, R, V, and Z, 2% L, I, E and K, 1% Q and W, and <1% M. The design also included three loop lengths in each loop. Overlap extension reactions of eight oligonucleotides were carried out separately to create full length tGp2 genes and avoid shorter loop length bias. Gene reactions were combined and transformed into yeast using homologous recombination with linearized yeast surface display vector. The total number of transformants was determined through serial dilution on SD-CAA plates (0.07 M sodium citrate (pH 5.3), yeast nitrogen base (6.7 g/L), casamino acids (5 g/L), and glucose (20 g/L)). Flow cytometry was used to determine the amount of full length tGp2 displayed, through labeling of the N-terminal HA epitope and C-terminal c-myc epitope, and supported with DNA sequence verification.

Binder Selection and Affinity Maturation

Selection and maturation of yeast was performed largely following a previously outlined protocol (Hackel et al. 2010. Protein Eng Des Sel 23:211-219). Briefly, yeast were grown to logarithmic phase in SD-CAA at 30° C., pelleted and resuspended to $1-3 \times 10^7$ cells/mL in SG-CAA (0.1M sodium phosphate, pH 6.0, 6.7 g/L yeast nitrogen base, 5 g/L casamino acids, 19 g/L galactose, 1 g/L glucose) and grown for 8-24 hours at 30° C. to induce protein expression. One round of magnetic sorting consisted of two negative selections, one for clones that do not bind streptavidin-coated magnetic beads, and one for clones that do not bind biotinylated control protein (either goat IgG, rabbit IgG, transferrin, or lysozyme) followed by a positive selection for clones that bind biotinylated target protein conjugated to streptavidin-coated magnetic beads. A round of flow cytometry sorting consisted of labeling the induced yeast library with 0.25 mg/L mouse anti-c-myc antibody (clone 9E10) and biotinylated target protein (concentration based on expected population binding strength), followed by fluorescent secondary labeling of fluorescein-conjugated goat anti-mouse antibody and Alexa Fluor 647-conjugated streptavidin. If clones were positive for target binding, represented by positive Alexa Fluor 647, and contained full length tGp2, represented by positive fluorescein signal, they were collected via fluorescence activated cell sorting (FACS). If no target binding was detected, all full length tGp2 clones were collected via FACS. The naïve library underwent two rounds of magnetic sorts (one wash at 4° C., three washes at 22° C.) and one flow cytometry sort. After the flow cytometry sort, plasmid DNA was extracted, mutagenized by error-prone PCR of the full gene or the diversified loops (both done in parallel), and retransformed into yeast. Mutagenized populations underwent two rounds of magnetic sorting (both containing three washes at 22° C.) and one flow cytometry sort. When dilution plating of the individual magnetic bead sorts indicated 5- to 10-fold more yeast collected during positive selection than yeast bound to the negative control protein conjugated beads, only one magnetic bead round (three washes at 22° C.) and one flow cytometry round were done for each mutagenized population.

tGp2 Production

The tGp2 gene was digested from the yeast surface display vector using NheI and BamHI restriction enzymes and ligated into a pET vector containing a C-terminal $His_6$ tag. The plasmid was transformed either into BL21 (DE3) or JE1 (DE3) E. coli and grown in LB medium (tryptone (10 g/L), yeast extract (5 g/L), and sodium chloride (10 g/L)) containing kanamycin (50 mg/L). One liter of LB medium with kanamycin was inoculated with 5 mL of overnight culture, grown to an optical density of 0.6-1.5 units at 37° C., and induced with 1 mM isopropyl β-D-1-thiogalactopyranoside (IPTG) for 20-24 hours at 30° C. Cells were pelleted, resuspended in 10 mL of lysis buffer (50 mM sodium phosphate (pH 8.0), 0.5 M NaCl, 5% glycerol, 5 mM CHAPS, and 25 mM imidazole), and underwent four freeze-thaw cycles. The soluble fraction was isolated by centrifugation at 12,000 g for 10 minutes, and tGp2 was purified by metal affinity chromatography on HisPur resin (Pierce, Thermo Fisher Scientific, Rockford, Ill.) and by reverse phase high performance liquid chromatography.

Affinity Measurement

The plasmid containing the clone of interest was transformed into yeast using the Frozen EZ Transformation Kit II (Zymo Research Corp., Irvine, Calif.), plated on SD medium plates and then grown directly in SG medium at 30° C. for at least 12 hours to induce protein expression. Cells were pelleted and washed with PBSA (phosphate buffered saline with 0.1% bovine serum albumin) and resuspended in PBSA containing biotin conjugated target over a range of concentrations. Sample volumes and cell densities were selected to ensure at least a 15-fold excess of target to displayed tGp2. The samples were incubated at 22° C. for an appropriate amount of time to reach 90% of the approach to equilibrium. After incubation, cells were washed and labeled with mouse anti-c-myc antibody (clone 9E10) for 10-15 minutes, washed, and labeled with fluorescein-conjugated goat anti-mouse antibody and Alexa Fluor 647-conjugated streptavidin for 10-15 minutes. Yeast were washed and Alexa Fluor 647 fluorescence was analyzed on a FACSCalibur flow cytometer (BD Biosciences, San Jose, Calif.). The relative fraction bound for cells displaying tGp2 was determined by subtracting background fluorescence of an unlabeled control and normalizing to the maximum saturated signal at high concentrations. The equilibrium dissociation constant, $K_D$, was identified as the concentration where half-maximal binding occurred.

Soluble affinity of select tGp2 proteins was determined using equilibrium competition titration, as described previously (Lipovsek et al., J Mol Biol, 2007, 368:1024-1041). Briefly, the soluble tGp2 clone was allowed sufficient time to reach 90% equilibrium with biotin-conjugated target over a range of tGp2 concentrations. Yeast cells displaying the same tGp2 clone and yeast cells harboring no plasmid (to aid in pelleting) were added to the solution, and allowed to equilibrate for six days. Cells were washed, labeled for target binding and analyzed with flow cytometry, as above.

Circular Dichroism

Purified tGp2 was lyophilized and resuspended in PBS to a concentration of 0.3-0.9 mg $mL^{-1}$. Ellipticity was measured from 260 to 200 nm on a Jasco J-815 spectrophotometer (Jasco, Inc., Easton, Md.) in a quartz cuvette with 1 mm path length. Thermal denaturation was carried out by measuring the ellipticity at 218 nm from 24° C. to 98° C. and $T_m$ was calculated from a standard two-state unfolding curve.

In Vitro Cell Labeling

A431 epidermoid carcinoma ($EGFR^{High}$), MDA-MB-231 breast carcinoma ($EGFR^{Mid}$), and MCF7 breast carcinoma ($EGFR^{Low}$) cells were incubated with varying concentrations of $tGp2$-EGFR-$His_6$ for 15 minutes or more at 4° C. Cells were pelleted, washed with PBSA, and labeled with fluorescein-conjugated rabbit anti-$His_6$ antibody for 15 minutes at 4° C. Cells were pelleted and washed, and analyzed on an Accuri C6 flow cytometer (BD Biosciences, San Jose, Calif.).

Alternatively, tGp2-EGFR-$His_6$ was biotinylated through a one hour, room temperature reaction with 30-fold molar excess EZ-Link NHS-PEG4-Biotin (Thermo Scientific, Waltham, Mass.) in PBS with 150 mM imidazole. Cell lines were labeled as above with biotinylated tGp2-EGFR-$His_6$. Except, Alexa Fluor 488-conjugated streptavidin was used as the secondary label.

Additionally, ligand specificity was examined through target blocking. 0.2 µM biotinylated tGp2-EGFR-$His_6$ and 2 µM unbiotinylated tGp2-EGFR-$His_6$ were co-incubated with A431 cells for 15 minutes. Cells were pelleted, washed, and labeled with Alexa Fluor 488-conjugated streptavidin for 15 minutes. After washing, flow cytometry was used to compare fluorescence of blocked and unblocked samples.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

Sequence Listing Free Text

SEQ ID NO: 1
KFWATVESSE HSFEVPVYAE TLDEALELAE WQYYPAGFEV TRVRP

SEQUENCE LISTING

```
<160> NUMBER OF SEQ ID NOS: 140

<210> SEQ ID NO 1
<211> LENGTH: 45
<212> TYPE: PRT
<213> ORGANISM: Enterobacteria phage T7

<400> SEQUENCE: 1

Lys Phe Trp Ala Thr Val Glu Ser Ser Glu His Ser Phe Glu Val Pro
1               5                   10                  15

Val Tyr Ala Glu Thr Leu Asp Glu Ala Leu Glu Leu Ala Glu Trp Gln
            20                  25                  30

Tyr Tyr Pro Ala Gly Phe Glu Val Thr Arg Val Arg Pro
        35                  40                  45

<210> SEQ ID NO 2
<211> LENGTH: 7
<212> TYPE: PRT
<213> ORGANISM: artificial
<220> FEATURE:
<223> OTHER INFORMATION: synthetic protein scaffold

<400> SEQUENCE: 2

Ser Arg Gly Asp Ser Tyr Trp
1               5

<210> SEQ ID NO 3
<211> LENGTH: 7
<212> TYPE: PRT
<213> ORGANISM: artificial
<220> FEATURE:
<223> OTHER INFORMATION: synthetic protein scaffold

<400> SEQUENCE: 3

Pro Met Tyr His Ile Tyr Tyr
1               5

<210> SEQ ID NO 4
```

```
<211> LENGTH: 8
<212> TYPE: PRT
<213> ORGANISM: artificial
<220> FEATURE:
<223> OTHER INFORMATION: synthetic protein scaffold

<400> SEQUENCE: 4

Tyr Ser Tyr Ala Gly Asn Phe Ala
1               5

<210> SEQ ID NO 5
<211> LENGTH: 8
<212> TYPE: PRT
<213> ORGANISM: artificial
<220> FEATURE:
<223> OTHER INFORMATION: synthetic protein scaffold

<400> SEQUENCE: 5

Pro Arg Ser Asn Tyr Trp Cys Leu
1               5

<210> SEQ ID NO 6
<211> LENGTH: 6
<212> TYPE: PRT
<213> ORGANISM: artificial
<220> FEATURE:
<223> OTHER INFORMATION: synthetic protein scaffold

<400> SEQUENCE: 6

Tyr Cys Ser Ser Asp Pro
1               5

<210> SEQ ID NO 7
<211> LENGTH: 8
<212> TYPE: PRT
<213> ORGANISM: artificial
<220> FEATURE:
<223> OTHER INFORMATION: synthetic protein scaffold

<400> SEQUENCE: 7

Gly Ser Asp Cys Phe Pro Leu Tyr
1               5

<210> SEQ ID NO 8
<211> LENGTH: 8
<212> TYPE: PRT
<213> ORGANISM: artificial
<220> FEATURE:
<223> OTHER INFORMATION: synthetic protein scaffold

<400> SEQUENCE: 8

Tyr Ser Phe Tyr Asp Asn Cys Leu
1               5

<210> SEQ ID NO 9
<211> LENGTH: 6
<212> TYPE: PRT
<213> ORGANISM: artificial
<220> FEATURE:
<223> OTHER INFORMATION: synthetic protein scaffold

<400> SEQUENCE: 9

Ser Pro Tyr Tyr Tyr Ser
1               5

<210> SEQ ID NO 10
<211> LENGTH: 7
```

```
<212> TYPE: PRT
<213> ORGANISM: artificial
<220> FEATURE:
<223> OTHER INFORMATION: synthetic protein scaffold

<400> SEQUENCE: 10

Pro Met Tyr His Val Tyr Tyr
1               5

<210> SEQ ID NO 11
<211> LENGTH: 8
<212> TYPE: PRT
<213> ORGANISM: artificial
<220> FEATURE:
<223> OTHER INFORMATION: synthetic protein scaffold

<400> SEQUENCE: 11

Tyr Asp Phe Val Ser Asn Cys Ile
1               5

<210> SEQ ID NO 12
<211> LENGTH: 7
<212> TYPE: PRT
<213> ORGANISM: artificial
<220> FEATURE:
<223> OTHER INFORMATION: synthetic protein scaffold

<400> SEQUENCE: 12

Ser Arg Gly Asp Ser His Trp
1               5

<210> SEQ ID NO 13
<211> LENGTH: 7
<212> TYPE: PRT
<213> ORGANISM: artificial
<220> FEATURE:
<223> OTHER INFORMATION: synthetic protein scaffold

<400> SEQUENCE: 13

Ser Arg Gly Gly Ser Tyr Trp
1               5

<210> SEQ ID NO 14
<211> LENGTH: 7
<212> TYPE: PRT
<213> ORGANISM: artificial
<220> FEATURE:
<223> OTHER INFORMATION: synthetic protein scaffold

<400> SEQUENCE: 14

Pro Thr Tyr His Ile Tyr Tyr
1               5

<210> SEQ ID NO 15
<211> LENGTH: 7
<212> TYPE: PRT
<213> ORGANISM: artificial
<220> FEATURE:
<223> OTHER INFORMATION: synthetic protein scaffold

<400> SEQUENCE: 15

Pro Met Tyr Tyr Ile Tyr Tyr
1               5

<210> SEQ ID NO 16
<211> LENGTH: 8
<212> TYPE: PRT
```

```
<213> ORGANISM: artificial
<220> FEATURE:
<223> OTHER INFORMATION: synthetic protein scaffold

<400> SEQUENCE: 16

Tyr Asp Tyr Asp Ala Asp Tyr Tyr
1               5

<210> SEQ ID NO 17
<211> LENGTH: 8
<212> TYPE: PRT
<213> ORGANISM: artificial
<220> FEATURE:
<223> OTHER INFORMATION: synthetic protein scaffold

<400> SEQUENCE: 17

Tyr Ser Asn His Ser Asp Tyr Leu
1               5

<210> SEQ ID NO 18
<211> LENGTH: 8
<212> TYPE: PRT
<213> ORGANISM: artificial
<220> FEATURE:
<223> OTHER INFORMATION: synthetic protein scaffold

<400> SEQUENCE: 18

His Cys Tyr Tyr Ala Asn Tyr Thr
1               5

<210> SEQ ID NO 19
<211> LENGTH: 8
<212> TYPE: PRT
<213> ORGANISM: artificial
<220> FEATURE:
<223> OTHER INFORMATION: synthetic protein scaffold

<400> SEQUENCE: 19

His Tyr Pro Asn Cys Ala Ile Tyr
1               5

<210> SEQ ID NO 20
<211> LENGTH: 8
<212> TYPE: PRT
<213> ORGANISM: artificial
<220> FEATURE:
<223> OTHER INFORMATION: synthetic protein scaffold

<400> SEQUENCE: 20

Tyr Ser Asn Arg Ser Asp Tyr Leu
1               5

<210> SEQ ID NO 21
<211> LENGTH: 8
<212> TYPE: PRT
<213> ORGANISM: artificial
<220> FEATURE:
<223> OTHER INFORMATION: synthetic protein scaffold

<400> SEQUENCE: 21

Arg Arg Asp Asn Asp Tyr Arg Tyr
1               5

<210> SEQ ID NO 22
<211> LENGTH: 7
<212> TYPE: PRT
<213> ORGANISM: artificial
```

```
<220> FEATURE:
<223> OTHER INFORMATION: synthetic protein scaffold

<400> SEQUENCE: 22

Pro Asp Trp Thr Ser Val Tyr
1               5

<210> SEQ ID NO 23
<211> LENGTH: 8
<212> TYPE: PRT
<213> ORGANISM: artificial
<220> FEATURE:
<223> OTHER INFORMATION: synthetic protein scaffold

<400> SEQUENCE: 23

His Cys Tyr Tyr Ala Asp Tyr Thr
1               5

<210> SEQ ID NO 24
<211> LENGTH: 8
<212> TYPE: PRT
<213> ORGANISM: artificial
<220> FEATURE:
<223> OTHER INFORMATION: synthetic protein scaffold

<400> SEQUENCE: 24

His Cys His Tyr Ala Asn Tyr Thr
1               5

<210> SEQ ID NO 25
<211> LENGTH: 8
<212> TYPE: PRT
<213> ORGANISM: artificial
<220> FEATURE:
<223> OTHER INFORMATION: synthetic protein scaffold

<400> SEQUENCE: 25

His Tyr Pro Asn Cys Ala Val Tyr
1               5

<210> SEQ ID NO 26
<211> LENGTH: 8
<212> TYPE: PRT
<213> ORGANISM: artificial
<220> FEATURE:
<223> OTHER INFORMATION: synthetic protein scaffold

<400> SEQUENCE: 26

His Tyr Pro Asn Cys Ala Ile His
1               5

<210> SEQ ID NO 27
<211> LENGTH: 8
<212> TYPE: PRT
<213> ORGANISM: artificial
<220> FEATURE:
<223> OTHER INFORMATION: synthetic protein scaffold

<400> SEQUENCE: 27

His Cys Asp Tyr Ala Asn Tyr Thr
1               5

<210> SEQ ID NO 28
<211> LENGTH: 8
<212> TYPE: PRT
<213> ORGANISM: artificial
<220> FEATURE:
```

```
<223> OTHER INFORMATION: synthetic protein scaffold

<400> SEQUENCE: 28

His Tyr Pro Asn Cys Val Ile Tyr
1               5

<210> SEQ ID NO 29
<211> LENGTH: 8
<212> TYPE: PRT
<213> ORGANISM: artificial
<220> FEATURE:
<223> OTHER INFORMATION: synthetic protein scaffold

<400> SEQUENCE: 29

His Cys Tyr Tyr Ala Asn Tyr Ala
1               5

<210> SEQ ID NO 30
<211> LENGTH: 8
<212> TYPE: PRT
<213> ORGANISM: artificial
<220> FEATURE:
<223> OTHER INFORMATION: synthetic protein scaffold

<400> SEQUENCE: 30

His Tyr Pro Asn Cys Ala Leu Tyr
1               5

<210> SEQ ID NO 31
<211> LENGTH: 8
<212> TYPE: PRT
<213> ORGANISM: artificial
<220> FEATURE:
<223> OTHER INFORMATION: synthetic protein scaffold

<400> SEQUENCE: 31

His Cys Ser Tyr Ala Asn Tyr Thr
1               5

<210> SEQ ID NO 32
<211> LENGTH: 8
<212> TYPE: PRT
<213> ORGANISM: artificial
<220> FEATURE:
<223> OTHER INFORMATION: synthetic protein scaffold

<400> SEQUENCE: 32

His Cys His Tyr Ala Asp Tyr Thr
1               5

<210> SEQ ID NO 33
<211> LENGTH: 8
<212> TYPE: PRT
<213> ORGANISM: artificial
<220> FEATURE:
<223> OTHER INFORMATION: synthetic protein scaffold

<400> SEQUENCE: 33

His Cys Tyr Tyr Ala Ser Tyr Thr
1               5

<210> SEQ ID NO 34
<211> LENGTH: 8
<212> TYPE: PRT
<213> ORGANISM: artificial
<220> FEATURE:
<223> OTHER INFORMATION: synthetic protein scaffold
```

```
<400> SEQUENCE: 34

Tyr Cys Tyr Tyr Ala Asn Tyr Thr
1               5

<210> SEQ ID NO 35
<211> LENGTH: 8
<212> TYPE: PRT
<213> ORGANISM: artificial
<220> FEATURE:
<223> OTHER INFORMATION: synthetic protein scaffold

<400> SEQUENCE: 35

Arg Cys Tyr Tyr Ala Asn Tyr Thr
1               5

<210> SEQ ID NO 36
<211> LENGTH: 8
<212> TYPE: PRT
<213> ORGANISM: artificial
<220> FEATURE:
<223> OTHER INFORMATION: synthetic protein scaffold

<400> SEQUENCE: 36

Tyr Asp Tyr Asp Ala Asp Cys Tyr
1               5

<210> SEQ ID NO 37
<211> LENGTH: 7
<212> TYPE: PRT
<213> ORGANISM: artificial
<220> FEATURE:
<223> OTHER INFORMATION: synthetic protein scaffold

<400> SEQUENCE: 37

Cys Pro Tyr His His Tyr Cys
1               5

<210> SEQ ID NO 38
<211> LENGTH: 8
<212> TYPE: PRT
<213> ORGANISM: artificial
<220> FEATURE:
<223> OTHER INFORMATION: synthetic protein scaffold

<400> SEQUENCE: 38

Tyr Ser Asp Arg Ser Asp Tyr Leu
1               5

<210> SEQ ID NO 39
<211> LENGTH: 8
<212> TYPE: PRT
<213> ORGANISM: artificial
<220> FEATURE:
<223> OTHER INFORMATION: synthetic protein scaffold

<400> SEQUENCE: 39

His Cys Tyr Tyr Ala Asn Tyr Ser
1               5

<210> SEQ ID NO 40
<211> LENGTH: 8
<212> TYPE: PRT
<213> ORGANISM: artificial
<220> FEATURE:
<223> OTHER INFORMATION: synthetic protein scaffold
```

```
<400> SEQUENCE: 40

His Tyr Pro Asn Cys Ala Ile Ser
1               5

<210> SEQ ID NO 41
<211> LENGTH: 8
<212> TYPE: PRT
<213> ORGANISM: artificial
<220> FEATURE:
<223> OTHER INFORMATION: synthetic protein scaffold

<400> SEQUENCE: 41

His Cys Asn Tyr Ala Asn Tyr Thr
1               5

<210> SEQ ID NO 42
<211> LENGTH: 8
<212> TYPE: PRT
<213> ORGANISM: artificial
<220> FEATURE:
<223> OTHER INFORMATION: synthetic protein scaffold

<400> SEQUENCE: 42

Tyr Ser Ser Arg Ser Asp Tyr Leu
1               5

<210> SEQ ID NO 43
<211> LENGTH: 8
<212> TYPE: PRT
<213> ORGANISM: artificial
<220> FEATURE:
<223> OTHER INFORMATION: synthetic protein scaffold

<400> SEQUENCE: 43

Arg Tyr Pro Asn Cys Ala Ile Tyr
1               5

<210> SEQ ID NO 44
<211> LENGTH: 6
<212> TYPE: PRT
<213> ORGANISM: artificial
<220> FEATURE:
<223> OTHER INFORMATION: synthetic protein scaffold

<400> SEQUENCE: 44

His Ser Val His Gly Tyr
1               5

<210> SEQ ID NO 45
<211> LENGTH: 6
<212> TYPE: PRT
<213> ORGANISM: artificial
<220> FEATURE:
<223> OTHER INFORMATION: synthetic protein scaffold

<400> SEQUENCE: 45

Gly Asn Ala Leu Gly Tyr
1               5

<210> SEQ ID NO 46
<211> LENGTH: 6
<212> TYPE: PRT
<213> ORGANISM: artificial
<220> FEATURE:
<223> OTHER INFORMATION: synthetic protein scaffold

<400> SEQUENCE: 46
```

His Asn Val Tyr Gly Tyr
1               5

<210> SEQ ID NO 47
<211> LENGTH: 8
<212> TYPE: PRT
<213> ORGANISM: artificial
<220> FEATURE:
<223> OTHER INFORMATION: synthetic protein scaffold

<400> SEQUENCE: 47

Arg Cys Asp His Tyr Pro Tyr Ser
1               5

<210> SEQ ID NO 48
<211> LENGTH: 6
<212> TYPE: PRT
<213> ORGANISM: artificial
<220> FEATURE:
<223> OTHER INFORMATION: synthetic protein scaffold

<400> SEQUENCE: 48

Arg Ser Asn Leu Leu Tyr
1               5

<210> SEQ ID NO 49
<211> LENGTH: 6
<212> TYPE: PRT
<213> ORGANISM: artificial
<220> FEATURE:
<223> OTHER INFORMATION: synthetic protein scaffold

<400> SEQUENCE: 49

Arg Ser Glu Asn Gly Ala
1               5

<210> SEQ ID NO 50
<211> LENGTH: 6
<212> TYPE: PRT
<213> ORGANISM: artificial
<220> FEATURE:
<223> OTHER INFORMATION: synthetic protein scaffold

<400> SEQUENCE: 50

Arg Ser Asp Leu Leu Tyr
1               5

<210> SEQ ID NO 51
<211> LENGTH: 6
<212> TYPE: PRT
<213> ORGANISM: artificial
<220> FEATURE:
<223> OTHER INFORMATION: synthetic protein scaffold

<400> SEQUENCE: 51

His Trp Asn Gly Asn Asp
1               5

<210> SEQ ID NO 52
<211> LENGTH: 8
<212> TYPE: PRT
<213> ORGANISM: artificial
<220> FEATURE:
<223> OTHER INFORMATION: synthetic protein scaffold

<400> SEQUENCE: 52

Tyr His Arg Asn His Ser Ile Pro
1               5

<210> SEQ ID NO 53
<211> LENGTH: 6
<212> TYPE: PRT
<213> ORGANISM: artificial
<220> FEATURE:
<223> OTHER INFORMATION: synthetic protein scaffold

<400> SEQUENCE: 53

Tyr Asn Asp Ser Tyr Tyr
1               5

<210> SEQ ID NO 54
<211> LENGTH: 6
<212> TYPE: PRT
<213> ORGANISM: artificial
<220> FEATURE:
<223> OTHER INFORMATION: synthetic protein scaffold

<400> SEQUENCE: 54

His Arg Gly Asp Ala Val
1               5

<210> SEQ ID NO 55
<211> LENGTH: 8
<212> TYPE: PRT
<213> ORGANISM: artificial
<220> FEATURE:
<223> OTHER INFORMATION: synthetic protein scaffold

<400> SEQUENCE: 55

Arg Cys Asp Arg Tyr Pro Tyr Ser
1               5

<210> SEQ ID NO 56
<211> LENGTH: 8
<212> TYPE: PRT
<213> ORGANISM: artificial
<220> FEATURE:
<223> OTHER INFORMATION: synthetic protein scaffold

<400> SEQUENCE: 56

Asn Tyr Ser Cys His Leu His Tyr
1               5

<210> SEQ ID NO 57
<211> LENGTH: 6
<212> TYPE: PRT
<213> ORGANISM: artificial
<220> FEATURE:
<223> OTHER INFORMATION: synthetic protein scaffold

<400> SEQUENCE: 57

Pro Tyr Asn Thr His Phe
1               5

<210> SEQ ID NO 58
<211> LENGTH: 8
<212> TYPE: PRT
<213> ORGANISM: artificial
<220> FEATURE:
<223> OTHER INFORMATION: synthetic protein scaffold

<400> SEQUENCE: 58

Pro Asn Ala Phe Cys Lys Tyr Cys

```
<210> SEQ ID NO 59
<211> LENGTH: 7
<212> TYPE: PRT
<213> ORGANISM: artificial
<220> FEATURE:
<223> OTHER INFORMATION: synthetic protein scaffold

<400> SEQUENCE: 59

Glu Ala Ala Cys Tyr Gly Trp
1               5

<210> SEQ ID NO 60
<211> LENGTH: 6
<212> TYPE: PRT
<213> ORGANISM: artificial
<220> FEATURE:
<223> OTHER INFORMATION: synthetic protein scaffold

<400> SEQUENCE: 60

His Asp Val Tyr Gly Tyr
1               5

<210> SEQ ID NO 61
<211> LENGTH: 6
<212> TYPE: PRT
<213> ORGANISM: artificial
<220> FEATURE:
<223> OTHER INFORMATION: synthetic protein scaffold

<400> SEQUENCE: 61

His Asn Ala Tyr Gly Tyr
1               5

<210> SEQ ID NO 62
<211> LENGTH: 6
<212> TYPE: PRT
<213> ORGANISM: artificial
<220> FEATURE:
<223> OTHER INFORMATION: synthetic protein scaffold

<400> SEQUENCE: 62

His Asn Val His Gly Tyr
1               5

<210> SEQ ID NO 63
<211> LENGTH: 6
<212> TYPE: PRT
<213> ORGANISM: artificial
<220> FEATURE:
<223> OTHER INFORMATION: synthetic protein scaffold

<400> SEQUENCE: 63

His Ser Val Tyr Gly Tyr
1               5

<210> SEQ ID NO 64
<211> LENGTH: 8
<212> TYPE: PRT
<213> ORGANISM: artificial
<220> FEATURE:
<223> OTHER INFORMATION: synthetic protein scaffold

<400> SEQUENCE: 64

Tyr Asp Phe Asp His Tyr Gly Tyr
1               5
```

```
<210> SEQ ID NO 65
<211> LENGTH: 6
<212> TYPE: PRT
<213> ORGANISM: artificial
<220> FEATURE:
<223> OTHER INFORMATION: synthetic protein scaffold

<400> SEQUENCE: 65

Arg Pro Gly Tyr Gly Tyr
1               5

<210> SEQ ID NO 66
<211> LENGTH: 6
<212> TYPE: PRT
<213> ORGANISM: artificial
<220> FEATURE:
<223> OTHER INFORMATION: synthetic protein scaffold

<400> SEQUENCE: 66

Gly Asp Ala Leu Gly Tyr
1               5

<210> SEQ ID NO 67
<211> LENGTH: 6
<212> TYPE: PRT
<213> ORGANISM: artificial
<220> FEATURE:
<223> OTHER INFORMATION: synthetic protein scaffold

<400> SEQUENCE: 67

Arg Gly Pro Tyr Gly Tyr
1               5

<210> SEQ ID NO 68
<211> LENGTH: 6
<212> TYPE: PRT
<213> ORGANISM: artificial
<220> FEATURE:
<223> OTHER INFORMATION: synthetic protein scaffold

<400> SEQUENCE: 68

Gly Ser Ala Leu Gly Tyr
1               5

<210> SEQ ID NO 69
<211> LENGTH: 8
<212> TYPE: PRT
<213> ORGANISM: artificial
<220> FEATURE:
<223> OTHER INFORMATION: synthetic protein scaffold

<400> SEQUENCE: 69

Tyr Asp Gly Asn Gly Asn Gly Tyr
1               5

<210> SEQ ID NO 70
<211> LENGTH: 7
<212> TYPE: PRT
<213> ORGANISM: artificial
<220> FEATURE:
<223> OTHER INFORMATION: synthetic protein scaffold

<400> SEQUENCE: 70

Arg Asp Asp Asp Tyr Gly Phe
1               5
```

```
<210> SEQ ID NO 71
<211> LENGTH: 6
<212> TYPE: PRT
<213> ORGANISM: artificial
<220> FEATURE:
<223> OTHER INFORMATION: synthetic protein scaffold

<400> SEQUENCE: 71

His Gly Pro Tyr Gly Tyr
1               5

<210> SEQ ID NO 72
<211> LENGTH: 6
<212> TYPE: PRT
<213> ORGANISM: artificial
<220> FEATURE:
<223> OTHER INFORMATION: synthetic protein scaffold

<400> SEQUENCE: 72

Arg Ala Asn Leu Leu Tyr
1               5

<210> SEQ ID NO 73
<211> LENGTH: 6
<212> TYPE: PRT
<213> ORGANISM: artificial
<220> FEATURE:
<223> OTHER INFORMATION: synthetic protein scaffold

<400> SEQUENCE: 73

His Arg Gly Asp Thr Val
1               5

<210> SEQ ID NO 74
<211> LENGTH: 8
<212> TYPE: PRT
<213> ORGANISM: artificial
<220> FEATURE:
<223> OTHER INFORMATION: synthetic protein scaffold

<400> SEQUENCE: 74

Tyr Asp Tyr Asp Ala Gly Tyr Tyr
1               5

<210> SEQ ID NO 75
<211> LENGTH: 6
<212> TYPE: PRT
<213> ORGANISM: artificial
<220> FEATURE:
<223> OTHER INFORMATION: synthetic protein scaffold

<400> SEQUENCE: 75

His Asp Val His Gly Tyr
1               5

<210> SEQ ID NO 76
<211> LENGTH: 7
<212> TYPE: PRT
<213> ORGANISM: artificial
<220> FEATURE:
<223> OTHER INFORMATION: synthetic protein scaffold

<400> SEQUENCE: 76

Lys Asp Leu His His Asn Tyr
1               5
```

```
<210> SEQ ID NO 77
<211> LENGTH: 6
<212> TYPE: PRT
<213> ORGANISM: artificial
<220> FEATURE:
<223> OTHER INFORMATION: synthetic protein scaffold

<400> SEQUENCE: 77

Gly Lys Ala Leu Gly Tyr
1               5

<210> SEQ ID NO 78
<211> LENGTH: 7
<212> TYPE: PRT
<213> ORGANISM: artificial
<220> FEATURE:
<223> OTHER INFORMATION: synthetic protein scaffold

<400> SEQUENCE: 78

Tyr Asn Gln His Phe Gly Tyr
1               5

<210> SEQ ID NO 79
<211> LENGTH: 7
<212> TYPE: PRT
<213> ORGANISM: artificial
<220> FEATURE:
<223> OTHER INFORMATION: synthetic protein scaffold

<400> SEQUENCE: 79

Trp Asp Ala Ser Asp Ser Phe
1               5

<210> SEQ ID NO 80
<211> LENGTH: 5
<212> TYPE: PRT
<213> ORGANISM: artificial
<220> FEATURE:
<223> OTHER INFORMATION: synthetic protein scaffold

<400> SEQUENCE: 80

Ser Tyr Cys Tyr Pro
1               5

<210> SEQ ID NO 81
<211> LENGTH: 6
<212> TYPE: PRT
<213> ORGANISM: artificial
<220> FEATURE:
<223> OTHER INFORMATION: synthetic protein scaffold

<400> SEQUENCE: 81

Pro His Tyr Arg His Leu
1               5

<210> SEQ ID NO 82
<211> LENGTH: 6
<212> TYPE: PRT
<213> ORGANISM: artificial
<220> FEATURE:
<223> OTHER INFORMATION: synthetic protein scaffold

<400> SEQUENCE: 82

Tyr His Tyr His Pro Phe
1               5

<210> SEQ ID NO 83
```

```
<211> LENGTH: 8
<212> TYPE: PRT
<213> ORGANISM: artificial
<220> FEATURE:
<223> OTHER INFORMATION: synthetic protein scaffold

<400> SEQUENCE: 83

Cys Gly Leu Arg Thr Pro Thr Cys
1               5

<210> SEQ ID NO 84
<211> LENGTH: 7
<212> TYPE: PRT
<213> ORGANISM: artificial
<220> FEATURE:
<223> OTHER INFORMATION: synthetic protein scaffold

<400> SEQUENCE: 84

Ser Tyr Cys Tyr Pro Tyr Cys
1               5

<210> SEQ ID NO 85
<211> LENGTH: 6
<212> TYPE: PRT
<213> ORGANISM: artificial
<220> FEATURE:
<223> OTHER INFORMATION: synthetic protein scaffold

<400> SEQUENCE: 85

Lys His Gly Asp Asn Ser
1               5

<210> SEQ ID NO 86
<211> LENGTH: 6
<212> TYPE: PRT
<213> ORGANISM: artificial
<220> FEATURE:
<223> OTHER INFORMATION: synthetic protein scaffold

<400> SEQUENCE: 86

Glu Tyr Gly Gly Lys Cys
1               5

<210> SEQ ID NO 87
<211> LENGTH: 8
<212> TYPE: PRT
<213> ORGANISM: artificial
<220> FEATURE:
<223> OTHER INFORMATION: synthetic protein scaffold

<400> SEQUENCE: 87

Lys Asp Pro Tyr Ser Arg Leu Met
1               5

<210> SEQ ID NO 88
<211> LENGTH: 6
<212> TYPE: PRT
<213> ORGANISM: artificial
<220> FEATURE:
<223> OTHER INFORMATION: synthetic protein scaffold

<400> SEQUENCE: 88

Glu Tyr Asp Gly Glu Ile
1               5

<210> SEQ ID NO 89
<211> LENGTH: 6
```

```
<212> TYPE: PRT
<213> ORGANISM: artificial
<220> FEATURE:
<223> OTHER INFORMATION: synthetic protein scaffold

<400> SEQUENCE: 89

Glu Asp Asp Gly Met Ile
1               5

<210> SEQ ID NO 90
<211> LENGTH: 6
<212> TYPE: PRT
<213> ORGANISM: artificial
<220> FEATURE:
<223> OTHER INFORMATION: synthetic protein scaffold

<400> SEQUENCE: 90

Cys Asp His Ser Asp Cys
1               5

<210> SEQ ID NO 91
<211> LENGTH: 6
<212> TYPE: PRT
<213> ORGANISM: artificial
<220> FEATURE:
<223> OTHER INFORMATION: synthetic protein scaffold

<400> SEQUENCE: 91

Cys Asp His Gly Asp Cys
1               5

<210> SEQ ID NO 92
<211> LENGTH: 6
<212> TYPE: PRT
<213> ORGANISM: artificial
<220> FEATURE:
<223> OTHER INFORMATION: synthetic protein scaffold

<400> SEQUENCE: 92

Gln Asp His Asp Leu Lys
1               5

<210> SEQ ID NO 93
<211> LENGTH: 6
<212> TYPE: PRT
<213> ORGANISM: artificial
<220> FEATURE:
<223> OTHER INFORMATION: synthetic protein scaffold

<400> SEQUENCE: 93

Tyr Tyr His Gly Asn Tyr
1               5

<210> SEQ ID NO 94
<211> LENGTH: 8
<212> TYPE: PRT
<213> ORGANISM: artificial
<220> FEATURE:
<223> OTHER INFORMATION: synthetic protein scaffold

<400> SEQUENCE: 94

Tyr Asn Tyr Arg Phe Pro Lys Tyr
1               5

<210> SEQ ID NO 95
<211> LENGTH: 7
<212> TYPE: PRT
```

```
<213> ORGANISM: artificial
<220> FEATURE:
<223> OTHER INFORMATION: synthetic protein scaffold

<400> SEQUENCE: 95

Ala His Ser Gly Tyr Tyr Arg
1               5

<210> SEQ ID NO 96
<211> LENGTH: 6
<212> TYPE: PRT
<213> ORGANISM: artificial
<220> FEATURE:
<223> OTHER INFORMATION: synthetic protein scaffold

<400> SEQUENCE: 96

Tyr Ser Asn His His Tyr
1               5

<210> SEQ ID NO 97
<211> LENGTH: 6
<212> TYPE: PRT
<213> ORGANISM: artificial
<220> FEATURE:
<223> OTHER INFORMATION: synthetic protein scaffold

<400> SEQUENCE: 97

Ala Gly Lys Asn Ser Tyr
1               5

<210> SEQ ID NO 98
<211> LENGTH: 6
<212> TYPE: PRT
<213> ORGANISM: artificial
<220> FEATURE:
<223> OTHER INFORMATION: synthetic protein scaffold

<400> SEQUENCE: 98

Lys His Gly Gly Asn Ser
1               5

<210> SEQ ID NO 99
<211> LENGTH: 6
<212> TYPE: PRT
<213> ORGANISM: artificial
<220> FEATURE:
<223> OTHER INFORMATION: synthetic protein scaffold

<400> SEQUENCE: 99

Phe Ser Tyr Gly Asn Leu
1               5

<210> SEQ ID NO 100
<211> LENGTH: 6
<212> TYPE: PRT
<213> ORGANISM: artificial
<220> FEATURE:
<223> OTHER INFORMATION: synthetic protein scaffold

<400> SEQUENCE: 100

Ser Gly Ala Tyr Glu Tyr
1               5

<210> SEQ ID NO 101
<211> LENGTH: 6
<212> TYPE: PRT
<213> ORGANISM: artificial
```

```
<220> FEATURE:
<223> OTHER INFORMATION: synthetic protein scaffold

<400> SEQUENCE: 101

Phe Ser Tyr Gly Lys Leu
1               5

<210> SEQ ID NO 102
<211> LENGTH: 6
<212> TYPE: PRT
<213> ORGANISM: artificial
<220> FEATURE:
<223> OTHER INFORMATION: synthetic protein scaffold

<400> SEQUENCE: 102

Ser Gly Lys Tyr Glu Tyr
1               5

<210> SEQ ID NO 103
<211> LENGTH: 6
<212> TYPE: PRT
<213> ORGANISM: artificial
<220> FEATURE:
<223> OTHER INFORMATION: synthetic protein scaffold

<400> SEQUENCE: 103

Ser Ser Tyr Gly Ser Leu
1               5

<210> SEQ ID NO 104
<211> LENGTH: 6
<212> TYPE: PRT
<213> ORGANISM: artificial
<220> FEATURE:
<223> OTHER INFORMATION: synthetic protein scaffold

<400> SEQUENCE: 104

Ser Gly Glu Tyr Glu His
1               5

<210> SEQ ID NO 105
<211> LENGTH: 6
<212> TYPE: PRT
<213> ORGANISM: artificial
<220> FEATURE:
<223> OTHER INFORMATION: synthetic protein scaffold

<400> SEQUENCE: 105

Lys Tyr Tyr Asp Arg Ile
1               5

<210> SEQ ID NO 106
<211> LENGTH: 8
<212> TYPE: PRT
<213> ORGANISM: artificial
<220> FEATURE:
<223> OTHER INFORMATION: synthetic protein scaffold

<400> SEQUENCE: 106

Phe Asp Trp Val Asn Gly Phe Tyr
1               5

<210> SEQ ID NO 107
<211> LENGTH: 7
<212> TYPE: PRT
<213> ORGANISM: artificial
<220> FEATURE:
```

```
<223> OTHER INFORMATION: synthetic protein scaffold

<400> SEQUENCE: 107

Thr Thr Asp Asn Tyr Tyr Asp
1               5

<210> SEQ ID NO 108
<211> LENGTH: 7
<212> TYPE: PRT
<213> ORGANISM: artificial
<220> FEATURE:
<223> OTHER INFORMATION: synthetic protein scaffold

<400> SEQUENCE: 108

Cys Asp Ala Tyr Arg Tyr Cys
1               5

<210> SEQ ID NO 109
<211> LENGTH: 6
<212> TYPE: PRT
<213> ORGANISM: artificial
<220> FEATURE:
<223> OTHER INFORMATION: synthetic protein scaffold

<400> SEQUENCE: 109

Asp Ser Asn Tyr Ser Ile
1               5

<210> SEQ ID NO 110
<211> LENGTH: 7
<212> TYPE: PRT
<213> ORGANISM: artificial
<220> FEATURE:
<223> OTHER INFORMATION: synthetic protein scaffold

<400> SEQUENCE: 110

Thr Cys Tyr Thr Asp Tyr Asp
1               5

<210> SEQ ID NO 111
<211> LENGTH: 6
<212> TYPE: PRT
<213> ORGANISM: artificial
<220> FEATURE:
<223> OTHER INFORMATION: synthetic protein scaffold

<400> SEQUENCE: 111

Phe Tyr Thr Ile Cys Asp
1               5

<210> SEQ ID NO 112
<211> LENGTH: 6
<212> TYPE: PRT
<213> ORGANISM: artificial
<220> FEATURE:
<223> OTHER INFORMATION: synthetic protein scaffold

<400> SEQUENCE: 112

Cys Asn Tyr Trp Asp Cys
1               5

<210> SEQ ID NO 113
<211> LENGTH: 6
<212> TYPE: PRT
<213> ORGANISM: artificial
<220> FEATURE:
<223> OTHER INFORMATION: synthetic protein scaffold
```

<400> SEQUENCE: 113

Cys Ser Asn Trp Arg Cys
1               5

<210> SEQ ID NO 114
<211> LENGTH: 8
<212> TYPE: PRT
<213> ORGANISM: artificial
<220> FEATURE:
<223> OTHER INFORMATION: synthetic protein scaffold

<400> SEQUENCE: 114

Cys Asp Ile Tyr Phe Phe Gly Cys
1               5

<210> SEQ ID NO 115
<211> LENGTH: 6
<212> TYPE: PRT
<213> ORGANISM: artificial
<220> FEATURE:
<223> OTHER INFORMATION: synthetic protein scaffold

<400> SEQUENCE: 115

Cys Asp Asp Phe Phe Thr
1               5

<210> SEQ ID NO 116
<211> LENGTH: 6
<212> TYPE: PRT
<213> ORGANISM: artificial
<220> FEATURE:
<223> OTHER INFORMATION: synthetic protein scaffold

<400> SEQUENCE: 116

Ser Ser Tyr Ser Gly Leu
1               5

<210> SEQ ID NO 117
<211> LENGTH: 6
<212> TYPE: PRT
<213> ORGANISM: artificial
<220> FEATURE:
<223> OTHER INFORMATION: synthetic protein scaffold

<400> SEQUENCE: 117

Ser Gly Gly Tyr Glu Tyr
1               5

<210> SEQ ID NO 118
<211> LENGTH: 7
<212> TYPE: PRT
<213> ORGANISM: artificial
<220> FEATURE:
<223> OTHER INFORMATION: synthetic protein scaffold

<400> SEQUENCE: 118

Ser Gly Glu Tyr Glu His Val
1               5

<210> SEQ ID NO 119
<211> LENGTH: 6
<212> TYPE: PRT
<213> ORGANISM: artificial
<220> FEATURE:
<223> OTHER INFORMATION: synthetic protein scaffold

<400> SEQUENCE: 119

Ser Ser Tyr Gly Asn Leu
1               5

<210> SEQ ID NO 120
<211> LENGTH: 6
<212> TYPE: PRT
<213> ORGANISM: artificial
<220> FEATURE:
<223> OTHER INFORMATION: synthetic protein scaffold

<400> SEQUENCE: 120

Phe Ser Tyr Gly Ser Leu
1               5

<210> SEQ ID NO 121
<211> LENGTH: 6
<212> TYPE: PRT
<213> ORGANISM: artificial
<220> FEATURE:
<223> OTHER INFORMATION: synthetic protein scaffold

<400> SEQUENCE: 121

Ser Ser Tyr Gly Arg Leu
1               5

<210> SEQ ID NO 122
<211> LENGTH: 6
<212> TYPE: PRT
<213> ORGANISM: artificial
<220> FEATURE:
<223> OTHER INFORMATION: synthetic protein scaffold

<400> SEQUENCE: 122

Tyr Ser Tyr Gly Ser Leu
1               5

<210> SEQ ID NO 123
<211> LENGTH: 6
<212> TYPE: PRT
<213> ORGANISM: artificial
<220> FEATURE:
<223> OTHER INFORMATION: synthetic protein scaffold

<400> SEQUENCE: 123

Ser Gly Lys Tyr Glu His
1               5

<210> SEQ ID NO 124
<211> LENGTH: 7
<212> TYPE: PRT
<213> ORGANISM: artificial
<220> FEATURE:
<223> OTHER INFORMATION: synthetic protein scaffold

<400> SEQUENCE: 124

Cys Asp Ile Tyr Phe Gly Cys
1               5

<210> SEQ ID NO 125
<211> LENGTH: 6
<212> TYPE: PRT
<213> ORGANISM: artificial
<220> FEATURE:
<223> OTHER INFORMATION: synthetic protein scaffold

<400> SEQUENCE: 125

```
Cys Ser Tyr Gly Ser Leu
1               5

<210> SEQ ID NO 126
<211> LENGTH: 6
<212> TYPE: PRT
<213> ORGANISM: artificial
<220> FEATURE:
<223> OTHER INFORMATION: synthetic protein scaffold

<400> SEQUENCE: 126

Ser Phe Cys Tyr Pro Cys
1               5

<210> SEQ ID NO 127
<211> LENGTH: 7
<212> TYPE: PRT
<213> ORGANISM: artificial
<220> FEATURE:
<223> OTHER INFORMATION: synthetic protein scaffold

<400> SEQUENCE: 127

Arg His Leu Ser Gly Gly Tyr
1               5

<210> SEQ ID NO 128
<211> LENGTH: 59
<212> TYPE: PRT
<213> ORGANISM: artificial
<220> FEATURE:
<223> OTHER INFORMATION: partial wild-type Gp2 protein

<400> SEQUENCE: 128

Thr Gly Ser Leu Ser Val Asp Asn Lys Lys Phe Trp Ala Thr Val Glu
1               5                   10                  15

Ser Ser Glu His Ser Phe Glu Val Pro Ile Tyr Ala Glu Thr Leu Asp
            20                  25                  30

Glu Ala Leu Glu Leu Ala Glu Trp Gln Tyr Val Pro Ala Gly Phe Glu
        35                  40                  45

Val Thr Arg Val Arg Pro Cys Val Ala Pro Lys
    50                  55

<210> SEQ ID NO 129
<211> LENGTH: 64
<212> TYPE: PRT
<213> ORGANISM: artificial
<220> FEATURE:
<223> OTHER INFORMATION: wild-type Gp2 protein

<400> SEQUENCE: 129

Met Ser Asn Val Asn Thr Gly Ser Leu Ser Val Asp Asn Lys Lys Phe
1               5                   10                  15

Trp Ala Thr Val Glu Ser Ser Glu His Ser Phe Glu Val Pro Val Tyr
            20                  25                  30

Ala Glu Thr Leu Asp Glu Ala Leu Glu Leu Ala Glu Trp Gln Tyr Val
        35                  40                  45

Pro Ala Gly Phe Glu Val Thr Arg Val Arg Pro Cys Val Ala Pro Lys
    50                  55                  60

<210> SEQ ID NO 130
<211> LENGTH: 45
<212> TYPE: PRT
<213> ORGANISM: artificial
```

```
<220> FEATURE:
<223> OTHER INFORMATION: sequence logo indicating amino acid frequency
      of Gp2 homologs
<220> FEATURE:
<221> NAME/KEY: MISC_FEATURE
<222> LOCATION: (2)..(2)
<223> OTHER INFORMATION: X can be Phe or Val
<220> FEATURE:
<221> NAME/KEY: MISC_FEATURE
<222> LOCATION: (3)..(3)
<223> OTHER INFORMATION: X can be Trp, Ile, Phe, or Leu
<220> FEATURE:
<221> NAME/KEY: MISC_FEATURE
<222> LOCATION: (4)..(4)
<223> OTHER INFORMATION: X can be Ala, Val, or Leu
<220> FEATURE:
<221> NAME/KEY: MISC_FEATURE
<222> LOCATION: (5)..(5)
<223> OTHER INFORMATION: X can be Thr, His, or Glu
<220> FEATURE:
<221> NAME/KEY: MISC_FEATURE
<222> LOCATION: (6)..(6)
<223> OTHER INFORMATION: X can be Val, Ile, Lue, or Glu
<220> FEATURE:
<221> NAME/KEY: MISC_FEATURE
<222> LOCATION: (7)..(7)
<223> OTHER INFORMATION: X can be Glu or Gln
<220> FEATURE:
<221> NAME/KEY: MISC_FEATURE
<222> LOCATION: (8)..(8)
<223> OTHER INFORMATION: X can be Gly, Ser, or Leu
<220> FEATURE:
<221> NAME/KEY: MISC_FEATURE
<222> LOCATION: (9)..(9)
<223> OTHER INFORMATION: X can be Ser, Gln, Val, Asn, or Phe
<220> FEATURE:
<221> NAME/KEY: MISC_FEATURE
<222> LOCATION: (10)..(10)
<223> OTHER INFORMATION: X can be Glu, Gly, Asp, Thr, or Val
<220> FEATURE:
<221> NAME/KEY: MISC_FEATURE
<222> LOCATION: (11)..(11)
<223> OTHER INFORMATION: X can be His, Gln, Thr, Glu, or Lys
<220> FEATURE:
<221> NAME/KEY: MISC_FEATURE
<222> LOCATION: (12)..(12)
<223> OTHER INFORMATION: X can be Ser or Glu
<220> FEATURE:
<221> NAME/KEY: MISC_FEATURE
<222> LOCATION: (13)..(13)
<223> OTHER INFORMATION: X can be Phe or Met
<220> FEATURE:
<221> NAME/KEY: MISC_FEATURE
<222> LOCATION: (16)..(16)
<223> OTHER INFORMATION: X can be Pro or Leu
<220> FEATURE:
<221> NAME/KEY: MISC_FEATURE
<222> LOCATION: (17)..(17)
<223> OTHER INFORMATION: X can be Val or Ile
<220> FEATURE:
<221> NAME/KEY: MISC_FEATURE
<222> LOCATION: (18)..(18)
<223> OTHER INFORMATION: X can be Phe or Tyr
<220> FEATURE:
<221> NAME/KEY: MISC_FEATURE
<222> LOCATION: (20)..(20)
<223> OTHER INFORMATION: X can be Glu, Arg, Thr, Lys, or Gly
<220> FEATURE:
<221> NAME/KEY: MISC_FEATURE
<222> LOCATION: (21)..(21)
<223> OTHER INFORMATION: X can be Ser, Thr, or Asp
<220> FEATURE:
<221> NAME/KEY: MISC_FEATURE
<222> LOCATION: (22)..(22)
<223> OTHER INFORMATION: X can be Leu or Ile
<220> FEATURE:
<221> NAME/KEY: MISC_FEATURE
<222> LOCATION: (23)..(23)
<223> OTHER INFORMATION: X can be Glu, Asp, or Gly
```

```
<220> FEATURE:
<221> NAME/KEY: MISC_FEATURE
<222> LOCATION: (24)..(24)
<223> OTHER INFORMATION: X can be Glu or Gln
<220> FEATURE:
<221> NAME/KEY: MISC_FEATURE
<222> LOCATION: (26)..(26)
<223> OTHER INFORMATION: X can be Leu, Ala, Asn, Thr, or Val
<220> FEATURE:
<221> NAME/KEY: MISC_FEATURE
<222> LOCATION: (27)..(27)
<223> OTHER INFORMATION: X can be Glu or Leu
<220> FEATURE:
<221> NAME/KEY: MISC_FEATURE
<222> LOCATION: (28)..(28)
<223> OTHER INFORMATION: X can be Leu, Trp, Gln, or Lys
<220> FEATURE:
<221> NAME/KEY: MISC_FEATURE
<222> LOCATION: (29)..(29)
<223> OTHER INFORMATION: X can be Ala, Ser, or Thr
<220> FEATURE:
<221> NAME/KEY: MISC_FEATURE
<222> LOCATION: (30)..(30)
<223> OTHER INFORMATION: X can be Glu or Gln
<220> FEATURE:
<221> NAME/KEY: MISC_FEATURE
<222> LOCATION: (31)..(31)
<223> OTHER INFORMATION: X can be Trp or Glu
<220> FEATURE:
<221> NAME/KEY: MISC_FEATURE
<222> LOCATION: (32)..(32)
<223> OTHER INFORMATION: X can be Gln, Ala, Glu, or His
<220> FEATURE:
<221> NAME/KEY: MISC_FEATURE
<222> LOCATION: (34)..(34)
<223> OTHER INFORMATION: X can be Val or Glu
<220> FEATURE:
<221> NAME/KEY: MISC_FEATURE
<222> LOCATION: (35)..(35)
<223> OTHER INFORMATION: X can be Pro, Asp, Ser, or Glu
<220> FEATURE:
<221> NAME/KEY: MISC_FEATURE
<222> LOCATION: (36)..(36)
<223> OTHER INFORMATION: X can be Ala or Gln
<220> FEATURE:
<221> NAME/KEY: MISC_FEATURE
<222> LOCATION: (38)..(38)
<223> OTHER INFORMATION: X can be Phe or Tyr
<220> FEATURE:
<221> NAME/KEY: MISC_FEATURE
<222> LOCATION: (39)..(39)
<223> OTHER INFORMATION: X can be Glu, Ala, Lys, or Val
<220> FEATURE:
<221> NAME/KEY: MISC_FEATURE
<222> LOCATION: (40)..(40)
<223> OTHER INFORMATION: X can be Val or Ile
<220> FEATURE:
<221> NAME/KEY: MISC_FEATURE
<222> LOCATION: (41)..(41)
<223> OTHER INFORMATION: X can be Thr, Asn, or Gly
<220> FEATURE:
<221> NAME/KEY: MISC_FEATURE
<222> LOCATION: (43)..(43)
<223> OTHER INFORMATION: X can be Ile or Val
<220> FEATURE:
<221> NAME/KEY: MISC_FEATURE
<222> LOCATION: (45)..(45)
<223> OTHER INFORMATION: X can be Phe or Glu

<400> SEQUENCE: 130

Lys Xaa Xaa Xaa Xaa Xaa Xaa Xaa Xaa Xaa Xaa Xaa Glu Val Xaa
1               5                   10                  15

Xaa Xaa Ala Xaa Xaa Xaa Xaa Xaa Ala Xaa Xaa Xaa Xaa Xaa Xaa
                20                  25                  30

Tyr Xaa Xaa Xaa Gly Xaa Xaa Xaa Xaa Arg Xaa Arg Xaa
            35                  40                  45
```

```
<210> SEQ ID NO 131
<211> LENGTH: 45
<212> TYPE: PRT
<213> ORGANISM: artificial
<220> FEATURE:
<223> OTHER INFORMATION: truncated Gp2 library design protein

<400> SEQUENCE: 131

Lys Phe Trp Ala Thr Val Glu Ser Ser Glu His Ser Phe Glu Val Pro
1               5                   10                  15

Ile Tyr Ala Glu Thr Leu Asp Glu Ala Leu Glu Leu Ala Glu Trp Gln
            20                  25                  30

Tyr Val Pro Ala Gly Phe Glu Val Thr Arg Val Arg Pro
        35                  40                  45

<210> SEQ ID NO 132
<211> LENGTH: 49
<212> TYPE: PRT
<213> ORGANISM: artificial
<220> FEATURE:
<223> OTHER INFORMATION: truncated Gp2 library design protein
<220> FEATURE:
<221> NAME/KEY: REPEAT
<222> LOCATION: (7)..(14)
<223> OTHER INFORMATION: may include one to eight amino acids
<220> FEATURE:
<221> NAME/KEY: REPEAT
<222> LOCATION: (36)..(43)
<223> OTHER INFORMATION: may include one to eight amino acids

<400> SEQUENCE: 132

Lys Phe Trp Ala Thr Val Xaa Xaa Xaa Xaa Xaa Xaa Xaa Xaa Phe Glu
1               5                   10                  15

Val Pro Val Tyr Ala Glu Thr Leu Asp Glu Ala Leu Glu Leu Ala Glu
            20                  25                  30

Trp Gln Tyr Xaa Xaa Xaa Xaa Xaa Xaa Xaa Xaa Val Thr Arg Val Arg
        35                  40                  45

Pro

<210> SEQ ID NO 133
<211> LENGTH: 6
<212> TYPE: PRT
<213> ORGANISM: artificial
<220> FEATURE:
<223> OTHER INFORMATION: synthetic protein scaffold

<400> SEQUENCE: 133

Glu Ser Ser Glu His Ser
1               5

<210> SEQ ID NO 134
<211> LENGTH: 6
<212> TYPE: PRT
<213> ORGANISM: artificial
<220> FEATURE:
<223> OTHER INFORMATION: synthetic protein scaffold

<400> SEQUENCE: 134

Val Pro Ala Gly Phe Glu
1               5

<210> SEQ ID NO 135
<211> LENGTH: 50
<212> TYPE: PRT
```

```
<213> ORGANISM: artificial
<220> FEATURE:
<223> OTHER INFORMATION: evolved Gp2 domain consensus sequence
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 135

Ala Ser Lys Phe Trp Ala Thr Val Xaa His Xaa Arg Xaa Ser Phe Glu
1               5                   10                  15

Val Pro Val Tyr Ala Glu Thr Leu Asp Glu Ala Leu Glu Leu Ala Glu
                20                  25                  30

Trp Gln Tyr Ser Tyr Cys Tyr Pro Tyr Cys Val Thr Arg Val Arg Pro
            35                  40                  45

Gly Ser
    50

<210> SEQ ID NO 136
<211> LENGTH: 51
<212> TYPE: PRT
<213> ORGANISM: artificial
<220> FEATURE:
<223> OTHER INFORMATION: evolved Gp2 domain sequence that binds soluble
      mesenchymal epithelial transition

<400> SEQUENCE: 136

Ala Ser Lys Phe Trp Ala Thr Val Trp Asp Ala Ser Asp Ser Ser Phe
1               5                   10                  15

Phe Glu Val Pro Val Tyr Ala Glu Thr Leu Asp Glu Ala Leu Glu Leu
                20                  25                  30

Ala Glu Trp Gln Tyr Ser Tyr Cys Tyr Pro Cys Val Thr Arg Val Arg
            35                  40                  45

Pro Gly Ser
    50

<210> SEQ ID NO 137
<211> LENGTH: 48
<212> TYPE: PRT
<213> ORGANISM: artificial
<220> FEATURE:
<223> OTHER INFORMATION: evolved Gp2 domain sequence that binds soluble
      mesenchymal epithelial transition

<400> SEQUENCE: 137

Ala Ser Phe Trp Ala Thr Val Pro His Tyr Arg His Leu Phe Glu Val
1               5                   10                  15

Pro Val Tyr Ala Glu Thr Leu Asp Glu Ala Leu Glu Leu Ala Glu Trp
                20                  25                  30

Gln Tyr Tyr His Tyr His Pro Phe Val Thr Arg Val Arg Pro Gly Ser
            35                  40                  45

<210> SEQ ID NO 138
<211> LENGTH: 52
<212> TYPE: PRT
<213> ORGANISM: artificial
<220> FEATURE:
```

<223> OTHER INFORMATION: evolved Gp2 domain sequence that binds soluble
      mesenchymal epithelial transition

<400> SEQUENCE: 138

Ala Ser Lys Phe Trp Ala Thr Val Cys Gly Leu Arg Thr Pro Thr Cys
1               5                   10                  15

Phe Glu Val Pro Val Tyr Ala Glu Thr Le

What is claimed is:

1. A non-naturally occurring protein scaffold comprising:
   a frame comprising at least 95% amino acid sequence identity to SEQ ID NO: 129, forming a plurality of structural domains comprising at least one β structure or at least one α helix; and
   a plurality of loop regions comprising an amino acid sequence that varies from a naturally-occurring loop region by at least one amino acid deletion, amino acid substitution, or amino acid addition, the loop regions conferring increased affinity for a pre-selected target compared to the naturally-occurring loop region amino acid sequence, at least one loop region comprising one of SEQ ID NOs: 2-127.

2. The protein scaffold of claim 1 wherein the frame comprises an α helix and at least two β structures.

3. The protein scaffold of claim 1, wherein the frame comprises amino acids 15-20, 27-47, or 54-59 of SEQ ID NO:129.

4. The protein scaffold of claim 1, wherein the frame comprises amino acids 15-20, 27-47, and 54-59 of SEQ ID NO:129.

5. A pharmaceutical composition comprising the protein scaffold of claim 1.

6. A detection composition comprising the protein scaffold of claim 1.

7. The detection composition of claim 6 further comprising a detectable marker.

8. The detection composition of claim 7 wherein the detectable marker comprises a radioactive isotope, a fluorescent marker, or a colorimetric marker.

9. The protein scaffold of claim 1 comprising a melting temperature, as measured by loss of secondary structure at 218 nm, of greater than 67° C.

* * * * *